US011147872B2

(12) United States Patent
Porro

(10) Patent No.: US 11,147,872 B2
(45) Date of Patent: Oct. 19, 2021

(54) MULTIVALENT GLYCOCONJUGATE VACCINES

(71) Applicant: BIOSYNTH S.R.L., Rapolano Terme (IT)

(72) Inventor: Massimo Porro, Rapolano Terme (IT)

(73) Assignee: BIOSYNTH S.R.L., Rapolano Terme (IT)

( * ) Notice: Subject to any disclaimer, the term of this patent is extended or adjusted under 35 U.S.C. 154(b) by 0 days.

(21) Appl. No.: 16/379,569

(22) Filed: Apr. 9, 2019

(65) Prior Publication Data

US 2019/0224310 A1    Jul. 25, 2019

Related U.S. Application Data

(62) Division of application No. 14/764,953, filed as application No. PCT/EP2014/051670 on Jan. 29, 2014, now Pat. No. 10,300,135.

(30) Foreign Application Priority Data

Jan. 31, 2013  (IT) .............................. MI2013A0142

(51) Int. Cl.
  *A61K 39/00*    (2006.01)
  *A61K 39/385*   (2006.01)
  *A61K 39/09*    (2006.01)
  *A61K 39/095*   (2006.01)
  *A61K 39/102*   (2006.01)

(52) U.S. Cl.
  CPC .......... *A61K 39/385* (2013.01); *A61K 39/092* (2013.01); *A61K 39/095* (2013.01); *A61K 39/102* (2013.01); *A61K 2039/55505* (2013.01); *A61K 2039/6037* (2013.01); *A61K 2039/645* (2013.01); *A61K 2039/70* (2013.01)

(58) Field of Classification Search
  USPC ...................................................... 424/179.1
  See application file for complete search history.

(56) References Cited

U.S. PATENT DOCUMENTS 471,179 A  *  12/1978  Porro ................... A61K 39/092
                                                    424/94.1
5,153,312 A  *  10/1992  Porro ................... A61K 39/092
                                                    530/405

FOREIGN PATENT DOCUMENTS

EP    1501542 A  *  7/2003  ........... A61K 39/092
EP    2425854 A1    3/2012

OTHER PUBLICATIONS

Information Disclosure Statement filed Oct. 26, 2015 in parent U.S. Appl. No. 14/764,953, filed Jul. 30, 2015.
Information Disclosure Statement filed Nov. 16, 2015 in parent U.S. Appl. No. 14/764,953, filed Jul. 30, 2015.

* cited by examiner

*Primary Examiner* — Jana A Hines
*Assistant Examiner* — Khatol S Shahnan Shah
(74) *Attorney, Agent, or Firm* — Hedman & Costigan, P.C.; James V. Costigan; Kathleen A. Costigan

(57) ABSTRACT

The present invention refers to new conjugate antigens expressing built-in multiple epitopes and to polyvalent glycoconjugate vaccines and formulations containing the same. In addition, the present invention concerns the use of these vaccines in particular for the protection of the human population, and in particular for the protection of the paediatric population from pulmonary and systemic infections due to *S. pneumoniae, N. meningitidis, H. influenzae, K. pneumoniae, M. tuberculosis, S. aureus*, or from intestinal infections due to *S. typhi, V. cholerae* and *E. coli*. The present invention additionally refers to new polyvalent glycoconjugate vaccines for the protection from *C. albicans* and *E. coli* systemic and genitourinary infections or for the protection from *M. bovis* infections in veterinary medicine.

7 Claims, 13 Drawing Sheets

Specification includes a Sequence Listing.

¹H-NMR spectrum of Ps6A and Ps6A-DAB derivative

CHANNEL A                               STORED TO BIN #   3

7.05

10.28
                  11.64
           ER 0
      DATA SAVED TO BIN #   3

FILE  1,    METHOD  0,     RUN   3     INDEX   3              BIN   3
      PEAK#       AREA%        RT       AREA BC
          1        7.2         7.05     43170 01
          2        8.12       10.39     48686 02
          3       84.68       11.64    507727 03

TOTAL      100.                  599583

FIG.13

FIG.14
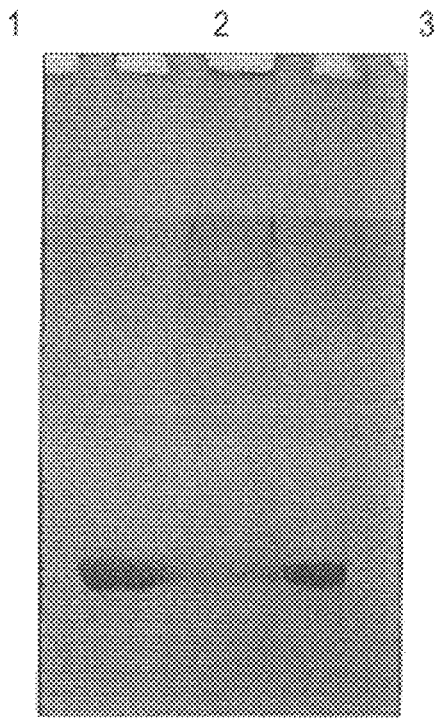
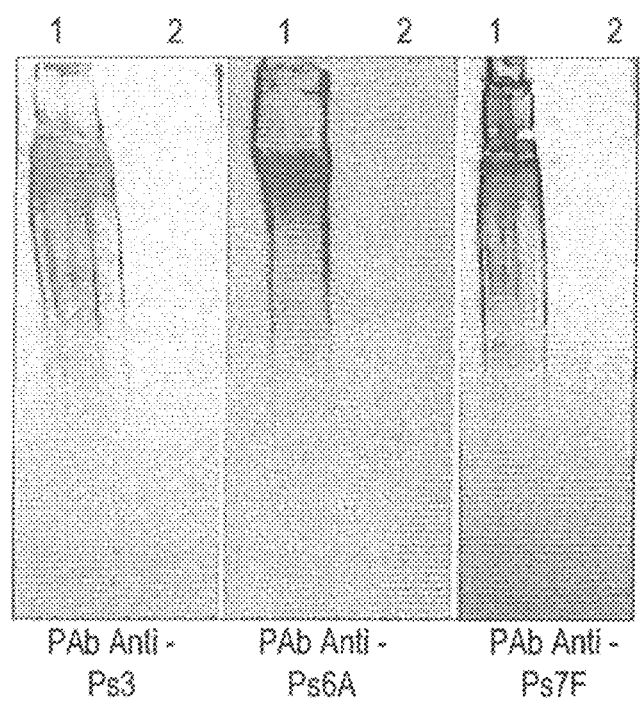
FIG.15

|  | 6A-DAB | CRM-3,6A,7F |
|---|---|---|
| LogEC50 | -0.2957 | -0.2820 |
| EC50 | 0.5061 | 0.5224 |

SEQUENCE LISTING

```
<160> NUMBER OF SEQ ID NOS: 7

<210> SEQ ID NO 1
<211> LENGTH: 535
<212> TYPE: PRT
<213> ORGANISM: Corynebacterium diphtheriae

<400> SEQUENCE: 1

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205
```

Ile Arg Asp Lys Thr Lys Thr Lys Ile Glu Ser Leu Lys Glu His Gly
210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
            245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
            275                 280                 285

Ile Asp Ser Glu Thr Ala Asp Asn Leu Glu Lys Thr Thr Ala Ala Leu
290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
            515                 520                 525

Leu Phe Phe Glu Ile Lys Ser
530                 535

<210> SEQ ID NO 2
<211> LENGTH: 538
<212> TYPE: PRT
<213> ORGANISM: Corynebacterium diphtheriae

<400> SEQUENCE: 2

```
Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
```

```
            35                  40                  45
Lys Pro Gly Tyr Val Asp Ser Ile Gln Lys Gly Ile Gln Lys Pro Lys
 50                  55                  60

Ser Gly Thr Gln Gly Asn Tyr Asp Asp Trp Lys Gly Phe Tyr Ser
 65                  70                  75                  80

Thr Asp Asn Lys Tyr Asp Ala Ala Gly Tyr Ser Val Asp Asn Glu Asn
                 85                  90                  95

Pro Leu Ser Gly Lys Ala Gly Val Val Lys Val Thr Tyr Pro Gly
                100                 105                 110

Leu Thr Lys Val Leu Ala Leu Lys Val Asp Asn Ala Glu Thr Ile Lys
                115                 120                 125

Lys Glu Leu Gly Leu Ser Leu Thr Glu Pro Leu Met Glu Gln Val Gly
                130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Val Glu Tyr Ile Asn
                165                 170                 175

Asn Trp Glu Gln Ala Lys Ala Leu Ser Val Glu Leu Glu Ile Asn Phe
                180                 185                 190

Glu Thr Arg Gly Lys Arg Gly Gln Asp Ala Met Tyr Glu Tyr Met Ala
                195                 200                 205

Gln Ala Cys Ala Gly Asn Arg Val Arg Arg Ser Val Gly Ser Ser Leu
                210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
                260                 265                 270

Glu Glu Phe His Gln Thr Ala Leu Glu His Pro Glu Leu Ser Glu Leu
                275                 280                 285

Lys Thr Val Thr Gly Thr Asn Pro Val Phe Ala Gly Ala Asn Tyr Ala
                290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
                340                 345                 350

Ile Val Ala Gln Ser Ile Ala Leu Ser Ser Leu Met Val Ala Gln Ala
                355                 360                 365

Ile Pro Leu Val Gly Glu Leu Val Asp Ile Gly Phe Ala Ala Tyr Asn
                370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Leu His
                405                 410                 415

Asp Gly Tyr Ala Val Ser Trp Asn Thr Val Glu Asp Ser Ile Ile Arg
                420                 425                 430

Thr Gly Phe Gln Gly Glu Ser Gly His Asp Ile Lys Ile Thr Ala Glu
                435                 440                 445

Asn Thr Pro Leu Pro Ile Ala Gly Val Leu Leu Pro Thr Ile Pro Gly
                450                 455                 460
```

-continued

```
Lys Leu Asp Val Asn Lys Ser Lys Thr His Ile Ser Val Asn Gly Arg
465                 470                 475                 480

Lys Ile Arg Met Arg Cys Arg Ala Ile Asp Gly Asp Val Thr Phe Cys
                485                 490                 495

Arg Pro Lys Ser Pro Val Tyr Val Gly Asn Gly Val His Ala Asn Leu
            500                 505                 510

His Val Ala Phe His Arg Ser Ser Glu Lys Ile His Ser Asn Glu
        515                 520                 525

Ile Ser Ser Asp Ser Ile Gly Val Leu Gly
530                 535

<210> SEQ ID NO 3
<211> LENGTH: 1260
<212> TYPE: PRT
<213> ORGANISM: Clostridium tetani

<400> SEQUENCE: 3

Arg Ile Pro Ile Thr Ile Asn Asn Phe Arg Tyr Ser Val Pro Val Asn
1               5                   10                  15

Asn Asp Thr Ile Ile Met Met Glu Pro Pro Tyr Cys Lys Gly Leu Asp
                20                  25                  30

Ile Tyr Tyr Lys Ala Phe Lys Ile Thr Asp Arg Ile Trp Ile Val Pro
            35                  40                  45

Glu Arg Tyr Glu Phe Gly Thr Lys Pro Glu Asp Phe Asn Pro Pro Ser
    50                  55                  60

Ser Leu Ile Glu Gly Ala Ser Glu Tyr Tyr Asp Pro Asn Tyr Leu Arg
65                  70                  75                  80

Thr Asp Ser Asp Lys Asp Arg Phe Leu Gln Thr Met Val Lys Leu Phe
                85                  90                  95

Asn Arg Ile Lys Asn Asn Val Ala Gly Glu Ala Leu Leu Asp Lys Ile
                100                 105                 110

Ile Asn Ala Ile Pro Tyr Leu Gly Asn Ser Tyr Ser Leu Leu Asp Lys
            115                 120                 125

Phe Asp Thr Asn Ser Asn Ser Val Ser Phe Asn Leu Ser Glu Gln Asp
130                 135                 140

Pro Ser Gly Ala Thr Thr Lys Ser Ala Met Leu Thr Ser Leu Ile Ile
145                 150                 155                 160

Phe Gly Pro Gly Pro Val Leu Asn Lys Asn Glu Val Arg Gly Ile Val
                165                 170                 175

Leu Arg Val Asp Asn Lys Asn Tyr Phe Pro Cys Arg Asp Gly Phe Gly
            180                 185                 190

Ser Ile Met Gln Met Thr Phe Cys Pro Glu Tyr Ile Pro Thr Phe Asp
    195                 200                 205

Asn Val Ile Glu Asn Ile Thr Ser Leu Thr Ile Gly Lys Ser Lys Tyr
210                 215                 220

Phe Gln Asp Pro Ala Leu Leu Leu Met His Glu Leu Ile His Val Leu
225                 230                 235                 240

His Gly Leu Tyr Gly Met Gln Val Ser Ser His Glu Ile Ile Pro Ser
                245                 250                 255

Lys Gln Glu Ile Tyr Met Gln His Thr Tyr Pro Ile Ser Ala Glu Glu
            260                 265                 270

Leu Phe Thr Phe Gly Gly Gln Asp Ala Asn Leu Ile Ser Ile Asp Ile
        275                 280                 285

Lys Asn Asp Leu Tyr Glu Lys Thr Leu Asn Asp Tyr Lys Ala Ile Ala
```

```
                  290                 295                 300
Asn Lys Leu Ser Gln Val Thr Ser Cys Asn Asp Pro Asn Ile Asp Ile
305                 310                 315                 320

Asp Ser Tyr Lys Gln Ile Tyr Gln Gln Lys Tyr Gln Phe Asp Lys Asp
                    325                 330                 335

Ser Asn Gly Gln Tyr Ile Val Asn Glu Asp Lys Phe Gln Ile Leu Tyr
                340                 345                 350

Asn Ser Ile Met Tyr Gly Phe Thr Glu Ile Glu Leu Gly Lys Lys Phe
            355                 360                 365

Asn Ile Lys Thr Arg Leu Ser Tyr Phe Ser Met Asn His Asp Pro Val
370                 375                 380

Lys Ile Pro Asn Leu Leu Asp Asp Thr Ile Tyr Asn Asp Thr Glu Gly
385                 390                 395                 400

Phe Asn Ile Glu Ser Lys Asp Leu Lys Ser Glu Tyr Lys Gly Gln Asn
                405                 410                 415

Met Arg Val Asn Thr Asn Ala Phe Arg Asn Val Asp Gly Ser Gly Leu
                420                 425                 430

Val Ser Lys Leu Ile Gly Leu Cys Lys Lys Ile Ile Pro Pro Thr Asn
            435                 440                 445

Ile Arg Glu Asn Leu Tyr Asn Arg Thr Ala Ala Leu Thr Asp Leu Gly
        450                 455                 460

Gly Glu Leu Cys Ile Lys Ile Lys Asn Glu Asp Leu Ile Phe Ile Ala
465                 470                 475                 480

Glu Lys Asn Ser Phe Ser Glu Glu Pro Phe Gln Asp Glu Ile Val Ser
                485                 490                 495

Tyr Asn Thr Lys Asn Lys Pro Leu Asn Phe Asn Tyr Ser Leu Asp Lys
                500                 505                 510

Ile Ile Leu Asp Tyr Asn Leu Gln Ser Lys Ile Thr Leu Pro Asn Asp
            515                 520                 525

Arg Thr Thr Pro Val Thr Lys Gly Ile Pro Tyr Ala Pro Glu Tyr Lys
        530                 535                 540

Ser Asn Ala Ala Ser Thr Ile Glu Ile His Asn Ile Asp Asp Asn Thr
545                 550                 555                 560

Ile Tyr Gln Tyr Leu Tyr Ala Gln Lys Ser Pro Thr Thr Leu Gln Arg
                565                 570                 575

Ile Thr Met Thr Asn Ser Val Asp Asp Ala Leu Ile Asn Ser Thr Lys
                580                 585                 590

Ile Tyr Ser Tyr Phe Pro Ser Val Ile Ser Lys Val Asn Gln Gly Ala
            595                 600                 605

Gln Gly Ile Leu Phe Leu Gln Trp Val Arg Asp Ile Ile Asp Asp Phe
        610                 615                 620

Thr Asn Glu Ser Ser Gln Lys Thr Thr Ile Asp Lys Ile Ser Asp Val
625                 630                 635                 640

Ser Thr Ile Val Pro Tyr Ile Gly Pro Ala Leu Asn Ile Val Lys Gln
                645                 650                 655

Gly Tyr Glu Gly Asn Phe Ile Gly Ala Leu Glu Thr Thr Gly Val Val
                660                 665                 670

Leu Leu Leu Glu Tyr Ile Pro Glu Ile Thr Leu Pro Val Ile Ala Ala
            675                 680                 685

Leu Ser Ile Ala Glu Ser Ser Thr Gln Lys Glu Lys Ile Ile Lys Thr
        690                 695                 700

Ile Asp Asn Phe Leu Glu Lys Arg Tyr Glu Lys Trp Ile Glu Val Tyr
705                 710                 715                 720
```

```
Lys Leu Val Lys Ala Lys Trp Leu Gly Thr Val Asn Thr Gln Phe Gln
            725                 730                 735
Lys Arg Ser Tyr Gln Met Tyr Arg Ser Leu Glu Tyr Gln Val Asp Ala
        740                 745                 750
Ile Lys Lys Ile Ile Asp Tyr Glu Tyr Lys Ile Tyr Ser Gly Pro Asp
        755                 760                 765
Lys Glu Gln Ile Ala Asp Glu Ile Asn Asn Leu Lys Asn Lys Leu Glu
        770                 775                 780
Glu Lys Ala Asn Lys Ala Met Ile Asn Ile Asn Ile Phe Met Arg Glu
785                 790                 795                 800
Ser Ser Arg Ser Phe Leu Val Asn Gln Met Ile Asn Glu Thr Lys Lys
            805                 810                 815
Gln Leu Leu Glu Phe Asp Thr Gln Ser Lys Asn Ile Leu Met Gln Tyr
            820                 825                 830
Ile Lys Ala Asn Ser Lys Phe Ile Gly Ile Thr Glu Leu Lys Lys Leu
            835                 840                 845
Glu Ser Lys Ile Asn Lys Val Phe Ser Thr Pro Ile Pro Phe Ser Tyr
            850                 855                 860
Ser Lys Asn Leu Asp Cys Trp Val Asp Asn Glu Glu Asp Ile Asp Val
865                 870                 875                 880
Ile Leu Lys Lys Ser Thr Ile Leu Asn Leu Asp Ile Asn Asn Asp Ile
                885                 890                 895
Ile Ser Asp Ile Ser Gly Phe Asn Ser Ser Val Ile Thr Tyr Pro Asp
                900                 905                 910
Ala Gln Leu Val Pro Gly Ile Asn Gly Lys Ala Ile His Leu Val Asn
            915                 920                 925
Asn Glu Ser Ser Glu Val Ile Val His Lys Ala Met Asp Ile Glu Tyr
            930                 935                 940
Asn Asp Met Phe Asn Asn Phe Thr Val Ser Phe Trp Leu Arg Val Pro
945                 950                 955                 960
Lys Val Ser Ala Ser His Leu Glu Gln Tyr Asp Thr Asn Glu Tyr Ser
                965                 970                 975
Ile Ile Ser Ser Met Lys Lys Tyr Ser Leu Ser Ile Gly Ser Gly Trp
                980                 985                 990
Ser Val Ser Leu Lys Gly Asn Asn  Leu Ile Trp Thr Leu Lys Asp Ser
            995                1000                1005
Ala Gly  Glu Val Arg Gln Ile  Thr Phe Arg Asp Leu  Ser Asp Lys
    1010                1015                1020
Phe Asn  Ala Tyr Leu Ala Asn  Lys Trp Val Phe Ile  Thr Ile Thr
    1025                1030                1035
Asn Asp Arg Leu Ser Ser Ala  Asn Leu Tyr Ile Asn  Gly Val Leu
    1040                1045                1050
Met Gly  Ser Ala Glu Ile Thr  Gly Leu Gly Ala Ile  Arg Glu Asp
    1055                1060                1065
Asn Asn  Ile Thr Leu Lys Leu  Asp Arg Cys Asn Asn  Asn Asn Gln
    1070                1075                1080
Tyr Val  Ser Ile Asp Lys Phe  Arg Ile Phe Cys Lys  Ala Leu Asn
    1085                1090                1095
Pro Lys  Glu Ile Glu Lys Leu  Tyr Thr Ser Tyr Leu  Ser Ile Thr
    1100                1105                1110
Phe Leu  Arg Asp Phe Trp Gly  Asn Pro Leu Arg Tyr  Asp Thr Glu
    1115                1120                1125
```

```
Tyr Tyr Leu Ile Pro Val Ala Tyr Ser Ser Lys Asp Val Gln Leu
    1130                1135                1140

Lys Asn Ile Thr Asp Tyr Met Tyr Leu Thr Asn Ala Pro Ser Tyr
    1145                1150                1155

Thr Asn Gly Lys Leu Asn Ile Tyr Tyr Arg Arg Leu Tyr Ser Gly
    1160                1165                1170

Leu Lys Phe Ile Ile Lys Arg Tyr Thr Pro Asn Glu Ile Asp
    1175                1180                1185

Ser Phe Val Arg Ser Gly Asp Phe Ile Lys Leu Tyr Val Ser Tyr
    1190                1195                1200

Asn Asn Asn Glu His Ile Val Gly Tyr Pro Lys Asp Gly Asn Ala
    1205                1210                1215

Phe Asn Asn Leu Asp Arg Ile Leu Arg Val Gly Tyr Asn Ala Pro
    1220                1225                1230

Gly Ile Pro Leu Tyr Lys Lys Met Glu Ala Val Lys Leu Arg Asp
    1235                1240                1245

Leu Lys Thr Tyr Ser Val Gln Leu Lys Leu Tyr Asp
    1250                1255                1260

<210> SEQ ID NO 4
<211> LENGTH: 364
<212> TYPE: PRT
<213> ORGANISM: Haemophilus influenzae

<400> SEQUENCE: 4

Met Lys Leu Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
                20                  25                  30

Ser Asp Lys Ile Ile Ile Ala His Arg Gly Ala Ser Gly Tyr Leu Pro
            35                  40                  45

Glu His Thr Leu Glu Ser Lys Ala Leu Ala Phe Ala Gln Gln Ala Asp
        50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                    85                  90                  95

Pro His Arg His Arg Lys Asp Gly Arg Tyr Tyr Val Ile Asp Phe Thr
                100                 105                 110

Leu Lys Glu Ile Gln Ser Leu Glu Met Thr Glu Asn Phe Glu Thr Lys
            115                 120                 125

Asp Gly Lys Gln Ala Gln Val Tyr Pro Asn Arg Phe Pro Leu Trp Lys
        130                 135                 140

Ser His Phe Arg Ile His Thr Phe Glu Asp Glu Ile Glu Phe Ile Gln
145                 150                 155                 160

Gly Leu Glu Lys Ser Thr Gly Lys Lys Val Gly Ile Tyr Pro Glu Ile
                    165                 170                 175

Lys Ala Pro Trp Phe His His Gln Asn Gly Lys Asp Ile Ala Ala Glu
                180                 185                 190

Thr Leu Lys Val Leu Lys Lys Tyr Gly Tyr Asp Lys Lys Thr Asp Met
            195                 200                 205

Val Tyr Leu Gln Thr Phe Asp Phe Asn Glu Leu Lys Arg Ile Lys Thr
        210                 215                 220

Glu Leu Leu Pro Gln Met Gly Met Asp Leu Lys Leu Val Gln Leu Ile
225                 230                 235                 240
```

```
Ala Tyr Thr Asp Trp Lys Glu Thr Gln Glu Lys Asp Pro Lys Gly Tyr
            245                 250                 255

Trp Val Asn Tyr Asn Tyr Asp Trp Met Phe Lys Pro Gly Ala Met Ala
            260                 265                 270

Glu Val Val Lys Tyr Ala Asp Gly Val Gly Pro Gly Trp Tyr Met Leu
            275                 280                 285

Val Asn Lys Glu Glu Ser Lys Pro Asp Asn Ile Val Tyr Thr Pro Leu
        290                 295                 300

Val Lys Glu Leu Ala Gln Tyr Asn Val Glu Val His Pro Tyr Thr Val
305                 310                 315                 320

Arg Lys Asp Ala Leu Pro Glu Phe Phe Thr Asp Val Asn Gln Met Tyr
                325                 330                 335

Asp Ala Leu Leu Asn Lys Ser Gly Ala Thr Gly Val Phe Thr Asp Phe
            340                 345                 350

Pro Asp Thr Gly Val Glu Phe Leu Lys Gly Ile Lys
            355                 360

<210> SEQ ID NO 5
<211> LENGTH: 609
<212> TYPE: PRT
<213> ORGANISM: Streptococcus pneumoniae

<400> SEQUENCE: 5

Met Asn Lys Lys Lys Met Ile Leu Thr Ser Leu Ala Ser Val Ala Ile
1               5                   10                  15

Leu Gly Ala Gly Phe Val Thr Ser Gln Pro Thr Phe Val Arg Ala Glu
            20                  25                  30

Glu Ala Pro Val Ala Ser Gln Ser Lys Ala Glu Lys Asp Tyr Asp Thr
        35                  40                  45

Ala Lys Arg Asp Ala Glu Asn Ala Lys Lys Ala Leu Glu Glu Ala Lys
    50                  55                  60

Arg Ala Gln Lys Lys Tyr Glu Asp Asp Gln Lys Lys Thr Glu Glu Lys
65                  70                  75                  80

Ala Lys Glu Glu Lys Gln Ala Ser Glu Ala Glu Gln Lys Ala Asn Leu
                85                  90                  95

Gln Tyr Gln Leu Lys Leu Arg Glu Tyr Ile Gln Lys Thr Gly Asp Arg
            100                 105                 110

Ser Lys Ile Gln Lys Glu Met Glu Glu Ala Glu Lys Lys His Lys Asn
        115                 120                 125

Ala Lys Ala Glu Phe Asp Lys Val Arg Gly Lys Val Ile Pro Ser Ala
    130                 135                 140

Glu Glu Leu Lys Glu Thr Arg Arg Lys Ala Glu Glu Ala Lys Ala Lys
145                 150                 155                 160

Glu Ala Glu Leu Thr Lys Lys Val Glu Ala Glu Lys Lys Val Thr
                165                 170                 175

Glu Ala Lys Gln Lys Leu Asp Ala Glu Arg Ala Lys Glu Val Ala Leu
            180                 185                 190

Gln Ala Lys Ile Ala Glu Leu Glu Asn Gln Val His Arg Leu Glu Thr
        195                 200                 205

Glu Leu Lys Glu Ile Asp Glu Ser Asp Ser Glu Asp Tyr Val Lys Glu
    210                 215                 220

Gly Leu Arg Val Pro Leu Gln Ser Glu Leu Asp Val Lys Gln Ala Lys
225                 230                 235                 240

Leu Ser Lys Leu Glu Glu Leu Ser Asp Lys Ile Asp Glu Leu Asp Ala
```

-continued

```
                        245                 250                 255
Glu Ile Ala Lys Leu Glu Lys Asp Val Glu Asp Phe Lys Asn Ser Asp
                260                 265                 270
Gly Glu Tyr Ser Ala Leu Tyr Leu Glu Ala Ala Glu Lys Asp Leu Val
            275                 280                 285
Ala Lys Lys Ala Glu Leu Glu Lys Thr Glu Ala Asp Leu Lys Lys Ala
        290                 295                 300
Val Asn Glu Pro Glu Lys Pro Ala Glu Pro Glu Asn Pro Ala Pro Ala
305                 310                 315                 320
Ala Pro Lys Pro Ala Pro Ala Pro Gln Pro Glu Lys Pro Ala Pro Ala
                325                 330                 335
Pro Ala Pro Lys Pro Glu Lys Ser Ala Asp Gln Gln Ala Glu Glu Asp
                340                 345                 350
Tyr Ala Arg Arg Ser Glu Glu Tyr Asn Arg Leu Thr Gln Gln Gln
            355                 360                 365
Pro Pro Lys Ala Glu Lys Pro Ala Pro Ala Pro Val Pro Lys Pro Glu
        370                 375                 380
Gln Pro Ala Pro Ala Pro Lys Thr Gly Trp Lys Gln Glu Asn Gly Met
385                 390                 395                 400
Trp Tyr Phe Tyr Asn Thr Asp Gly Ser Met Ala Thr Gly Trp Leu Gln
                405                 410                 415
Asn Asn Gly Ser Trp Tyr Tyr Leu Asn Ser Asn Gly Ala Met Ala Thr
            420                 425                 430
Gly Trp Leu Gln Tyr Asn Gly Ser Trp Tyr Tyr Leu Asn Ala Asn Gly
        435                 440                 445
Ala Met Ala Thr Gly Trp Ala Lys Val Asn Gly Ser Trp Tyr Tyr Leu
    450                 455                 460
Asn Ala Asn Gly Ala Met Ala Thr Gly Trp Leu Gln Tyr Asn Gly Ser
465                 470                 475                 480
Trp Tyr Tyr Leu Asn Ala Ser Gly Ala Met Ala Thr Gly Trp Ala Lys
                485                 490                 495
Val Asn Gly Ser Trp Tyr Tyr Leu Asn Ala Asn Gly Ser Met Ala Thr
            500                 505                 510
Gly Trp Leu Gln Tyr Asn Gly Ser Trp Tyr Tyr Leu Asn Ala Asn Gly
        515                 520                 525
Ala Met Ala Thr Gly Trp Ala Lys Val Asn Gly Ser Trp Tyr Tyr Leu
    530                 535                 540
Asn Ala Asn Gly Ser Met Ala Thr Gly Trp Val Lys Asp Gly Asp Thr
545                 550                 555                 560
Trp Tyr Tyr Leu Glu Ala Ser Gly Ala Met Lys Ala Ser Gln Trp Phe
                565                 570                 575
Lys Val Ser Asp Lys Trp Tyr Tyr Val Asn Gly Leu Gly Ala Leu Ala
            580                 585                 590
Val Asn Thr Thr Val Asp Gly Tyr Glu Val Asn Ala Asn Gly Glu Trp
        595                 600                 605
Val
```

<210> SEQ ID NO 6
<211> LENGTH: 769
<212> TYPE: PRT
<213> ORGANISM: Streptococcus pneumoniae

<400> SEQUENCE: 6

Met Phe Lys Ser Asn Tyr Glu Arg Lys Met Cys Tyr Ser Ile Arg Lys

```
1               5                   10                  15
Phe Ser Ile Gly Val Ala Ser Val Ala Ser Leu Val Met Gly
            20                  25                  30

Ser Val Val His Ala Thr Glu Asn Glu Gly Thr Thr Gln Ala Pro Thr
            35                  40                  45

Ser Ser Asn Arg Gly Asn Glu Ser Gln Ala Glu Gln Arg Arg Glu Leu
        50                  55                  60

Asp Leu Glu Arg Asp Lys Val Lys Lys Glu Val Arg Glu Tyr Lys Glu
65                  70                  75                  80

Lys Lys Val Lys Glu Leu Tyr Ser Lys Ser Thr Lys Ser Arg His Lys
                85                  90                  95

Lys Thr Val Asp Ile Val Asn Lys Leu Gln Asn Ile Asn Asn Glu Tyr
                100                 105                 110

Leu Asn Lys Ile Ile Gln Ser Thr Ser Thr Tyr Glu Glu Leu Gln Lys
            115                 120                 125

Leu Met Met Glu Ser Gln Ser Glu Val Asp Lys Ala Val Ser Glu Phe
        130                 135                 140

Glu Lys Asp Leu Ser Ser Ser Ser Ser Gly Ser Ser Thr Glu Pro
145                 150                 155                 160

Glu Ala Ser Asp Thr Ala Lys Pro Asn Lys Pro Thr Glu Leu Glu Lys
                165                 170                 175

Lys Val Ala Glu Ala Gln Gln Lys Val Glu Ala Glu Lys Lys Ala
            180                 185                 190

Lys Asp Gln Lys Glu Glu Asp Tyr Arg Asn Tyr Pro Thr Ile Thr Tyr
            195                 200                 205

Lys Thr Leu Glu Leu Glu Ile Ala Glu Phe Asp Val Lys Val Lys Glu
        210                 215                 220

Ala Glu Leu Glu Leu Val Lys Val Lys Ala Lys Glu Ser Arg Asp Glu
225                 230                 235                 240

Lys Lys Ile Lys Gln Ala Glu Ala Glu Val Glu Ser Lys Gln Ala Glu
                245                 250                 255

Ala Thr Arg Leu Lys Lys Ile Lys Thr Asp Arg Lys Lys Ala Glu Glu
            260                 265                 270

Glu Ala Lys Leu Lys Glu Ala Val Glu Lys Asn Ala Ala Thr Ser Glu
        275                 280                 285

Gln Gly Lys Pro Lys Arg Arg Val Lys Arg Gly Ala Leu Gly Glu Gln
    290                 295                 300

Ala Thr Pro Asp Lys Lys Asp Tyr Phe Glu Lys Asp Phe Arg Pro Ala
305                 310                 315                 320

Phe Asn Lys Asn Gln Gln Met Val Ala Ile Gln Glu Ser Leu Asn Lys
                325                 330                 335

Leu Asp Gly Glu Thr Lys Thr Val Pro Asp Gly Ala Lys Leu Thr Gly
            340                 345                 350

Glu Ala Gly Asn Ala Tyr Asn Glu Val Arg Asp Tyr Ala Ile Lys Val
        355                 360                 365

Val Ser Glu Asn Lys Lys Leu Leu Ser Gln Thr Ala Val Thr Met Asp
    370                 375                 380

Glu Leu Ala Met Gln Leu Thr Lys Leu Asn Asp Ala Met Ser Lys Leu
385                 390                 395                 400

Arg Glu Ala Lys Ala Lys Leu Val Pro Glu Val Lys Pro Gln Pro Glu
                405                 410                 415

Asn Pro Glu His Gln Arg Pro Thr Thr Pro Ala Pro Asp Thr Lys Pro
            420                 425                 430
```

```
Ile Pro Gln Pro Glu Gly Lys Lys Pro Ser Val Pro Asp Ile Asn Gln
        435                 440                 445

Glu Lys Glu Lys Ala Lys Leu Ala Val Ala Thr Tyr Met Ser Lys Ile
    450                 455                 460

Leu Asp Asp Ile Gln Lys His His Leu Gln Lys Glu Lys His Arg Gln
465                 470                 475                 480

Ile Val Ala Leu Ile Lys Glu Leu Asp Glu Phe Lys Lys Gln Ala Leu
                485                 490                 495

Ser Glu Ile Asp Asn Val Asn Thr Lys Val Glu Ile Glu Asn Thr Val
                500                 505                 510

His Lys Ile Phe Ala Asp Met Asp Ala Val Val Thr Lys Phe Lys Lys
            515                 520                 525

Gly Leu Thr Gln Asp Thr Pro Lys Glu Pro Asp Asn Lys Lys Pro Ser
        530                 535                 540

Ala Pro Lys Pro Gly Met Gln Pro Ser Pro Gln Pro Glu Gly Lys Lys
545                 550                 555                 560

Pro Ser Val Pro Ala Gln Pro Gly Thr Glu Asp Lys Lys Pro Ser Ala
                565                 570                 575

Pro Lys Pro Gly Met Gln Pro Ser Pro Gln Pro Glu Gly Lys Lys Pro
            580                 585                 590

Ser Val Pro Ala Gln Pro Gly Thr Glu Asp Lys Lys Pro Ser Ala Pro
        595                 600                 605

Lys Pro Asp Met Gln Pro Ser Pro Gln Pro Glu Gly Lys Lys Pro Ser
    610                 615                 620

Val Pro Ala Gln Pro Gly Thr Glu Asp Lys Lys Pro Ser Ala Pro Lys
625                 630                 635                 640

Pro Gly Met Gln Pro Ser Pro Gln Pro Glu Gly Lys Lys Pro Ser Val
                645                 650                 655

Pro Ala Gln Pro Gly Thr Glu Asp Lys Lys Pro Ser Ala Pro Lys Pro
            660                 665                 670

Asp Met Gln Pro Ser Pro Gln Pro Glu Gly Lys Lys Pro Ser Val Pro
        675                 680                 685

Ala Gln Pro Gly Thr Glu Asp Lys Lys Pro Ser Ala Pro Lys Pro Asp
    690                 695                 700

Met Gln Pro Ser Pro Gln Pro Glu Gly Lys Lys Pro Ser Val Pro Glu
705                 710                 715                 720

Ile Asn Gln Glu Lys Glu Lys Ala Lys Leu Ala Val Ala Thr Glu Lys
                725                 730                 735

Lys Leu Pro Ser Thr Gly Val Ala Ser Asn Leu Val Leu Glu Ile Ile
            740                 745                 750

Gly Leu Leu Gly Leu Ile Gly Thr Ser Phe Ile Ala Met Lys Arg Arg
        755                 760                 765

Lys

<210> SEQ ID NO 7
<211> LENGTH: 471
<212> TYPE: PRT
<213> ORGANISM: Streptococcus pneumoniae

<400> SEQUENCE: 7

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30
```

```
Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
 50                  55                  60

Thr Asn Asp Ser Arg Leu Tyr Pro Gly Ala Leu Leu Val Val Asp Glu
 65                  70                  75                  80

Thr Leu Leu Glu Asn Asn Pro Thr Leu Leu Ala Val Asp Arg Ala Pro
                 85                  90                  95

Met Thr Tyr Ser Ile Asp Leu Pro Gly Leu Ala Ser Ser Asp Ser Phe
                100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
            130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
                180                 185                 190

Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
            290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
                355                 360                 365

Gly Ala Tyr Val Ala Gln Tyr Tyr Ile Thr Trp Asn Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
435                 440                 445
```

```
Arg Lys Arg Thr Ile Ser Ile Trp Gly Thr Thr Leu Tyr Pro Gln Val
    450             455             460

Glu Asp Lys Val Glu Asn Asp
465             470
```

MULTIVALENT GLYCOCONJUGATE VACCINES

This application is a divisional application of Ser. No. 14/764,953, filed Jul. 30, 2015 which is a national stage of PCT/EP2014/051670, filed Jan. 29, 2014 which claims the priority of Italian Application MI2013A000142, filed Jan. 31, 2013.

The present invention refers to new conjugate antigens expressing built-in multiple epitopes and to polyvalent glycoconjugate vaccines and formulations containing the same. In addition, the present invention concerns the use of these vaccines in particular for the protection of the human population, and in particular for the protection of the paediatric population from pulmonary and systemic infections due to *S. pneumoniae, N. meningitidis, H. influenzae, K. pneumoniae, M. tuberculosis, S. aureus*, or from intestinal infections due to *S. typhi, V. cholerae* and *E. coli*. The present invention additionally refers to new polyvalent glycoconjugate vaccines for the protection from *C. albicans* and *E. coli* systemic and genitourinary infections or for the protection from *M. bovis* infections in veterinary medicine.

Conjugate vaccines are the golden standard for measuring the nowadays success of clinical immunology. Since the early Ninety's, the advent of conjugate vaccines for prevention of *H. influenzae, N. meningitidis* and *S. pneumoniae* have dramatically improved the quality of life of the paediatric population in the western World. Such an outstanding success is now going to be extended to the countries of the developing world thanks to the Immunization Expanded Program sponsored by WHO and the recently implemented national immunization programs through the Advance Market Commitment (AMC) of several countries.

For instance, vaccines like "Prevnar", present in the western markets since the year 2000 (formerly in its 7-valent formulation and now in its 13-valent formulation, both formulations containing single type-specific polysaccharide (Ps) of *S. pneumoniae* covalently conjugated to the carrier protein CRM197) is nowadays recommended by WHO to all countries of the world for an unprecedented campaign of immunization for the protection of the paediatric population from the systemic infections due to *S. pneumoniae* (IPD or Invasive Pneumococcal Diseases) which may ultimately induce acute bacterial meningitis. Indeed, this pathology is well documented as having a high mortality rate just because the time-interval of treatment is reduced to few hours from the beginning of the symptoms, so that the rational strategy to follow is the prevention and not the therapy of the disease.

Because the amount of bacterial species significantly representative for the infections in humans by *S. pneumoniae* are many (up to 23 bacterial species out of the more than 90 species today known) and the strategy of using single type-specific Ps conjugated to a protein carrier demands a significant dosage of the carrier protein when the vaccine formulation contains several conjugated antigens (e.g.: 13 or 15 or more if including the most epidemiologically important serotypes indicated by WHO as being drug resistant, which include the bacterial serotypes (according to the Danish nomenclature) 1, 2, 3, 4, 5, 6A, 6B, 6C, 7F, 8, 9N, 9V, 10A, 11A, 12F, 14, 15B, 17F, 18C, 19A, 19F, 20, 22F, 23F, 33F) the possibility to reduce the amount of the carrier protein in the whole conjugate formulations is becoming a prioritary issue.

In fact, one must consider that a child undertaking immunization with the conjugate vaccines of *H. influenzae* (one type-specific conjugate of type b Ps), *N. meningitidis* (four group-specific conjugates of group A, C, W135 and Y Ps) and *S. pneumoniae* (up-to thirteen type-specific conjugates of type 1, 3, 4, 5, 6A, 6B, 7F, 9V, 14, 18C, 19A, 19F, 23F Ps) for the prevention of broad-spectrum IPD, is going to be injected with eighteen conjugated antigens which have the relevant burden of eighteen times the single, type-specific, dose of carrier protein.

Furthermore, this dosage must be multiplied by three to four times, in consideration of the fact that three to four doses of the vaccines are necessary to confer full protection to the child in the first 2 years of age. All considered, the whole amount of carrier protein injected in a child, easily may reach doses of about 0.20 mg, at least in the case of the protein CRM197, with an obvious stress of the immune system which, however, so far seems to well tolerate such an amount of protein carrier for conferring helper T-cell dependency to the host. However, by continuously up-grading the formulation of polyvalent vaccines like the one for prevention of *S. pneumoniae* infections, the amount of serotype Ps, ergo of carrier protein, is destined to climb over time.

In this regard, the author of the present invention has found a new category of conjugate antigens which feature the expression of multiple carbohydrate specificities, predetermined and built-in the molecular construct, which uses one mole (or micromole or nanomole or picomole, all representative for a fraction of it) of protein carrier for carrying at least one mole (or micromole or nanomole or picomole, all representative for a fraction of it) of each of at least three different type (or group)-specific carbohydrate antigens, therefore a conjugate expressing at least a total of four different antigen-related serological specificities.

In this way, a vaccine formulation encompassing as many as eighteen type-specific conjugate antigens, as an example, will be synthesized by only using one third (or 33%) of the amount of carrier protein needed in the nowadays available single-antigen-associated formulation, so that the immunogenic burden on the immune-system of the host will be significantly lower and, consequently, safer.

It is in fact well known in immunology, the existence of the phenomenon defined as "carrier protein-dependent immune-suppression and immune interference" due to the down-regulation of the immune system which becomes overwhelmed by the amount of protein antigen administered in repeated doses, for instance as a conjugate entity, especially when significant serological titers of pre-existing, carrier protein-specific, memory IgG antibodies, are present in the treated host (Dagan R. et al., Vaccine 28 (34): 5513-5523, 2010). The significant reduction of the protein carrier dosage by the present molecular model, however, warrants the full expression of helper T-dependency, according to the previous experimental work pointing out that the anamnestic IgG immune response of mammalians towards a glycoconjugate antigen, is restricted to the hybrid linking area of the protein-carbohydrate epitopes with the specificity of the immune response confined to few monosaccharide residues of the covalently linked carbohydrate structure (Arndt and Porro, Immunobiology of Proteins and Peptides, Edited by M. Z. Atassi, Plenum Press, New York and London, Vol. 303, pages 129-148, 1991).

The above mentioned paper investigates on different chemical strategies and different MW of the Ps of *S. pneumoniae* conjugated to the carrier protein CRM197, for obtaining the optimal conjugate structure when using mono functionally-activated carbohydrate antigens; also, the paper investigates the most likely molecular area in the conjugate construct for being responsible of the helper-T dependency in mammalians (through the analysis of the IgG isotype polyclonal antibodies) by molecular mapping of the conjugates synthesized.

U.S. Pat. No. 4,711,779 in the name of the same applicant discloses a molecular model of tri-valent glycoprotein expressing immunogenicity in mammalians against a Gram-positive and a Gram-negative bacterium. The document referred to a molecular construct which used oligosaccharides of low MW, covalently coupled to the carrier protein via a linker derivative introduced at the end-reducing group discovered after chemical hydrolysis at low temperature; that conjugate featured a maximum of three different specificities (to the Protein CRM197, to Ps type 6A, to Ps group C); it used mono-functional oligosaccharides; the molecular construct induced serological specificity to the carrier protein and to each of the two carried carbohydrate structures.

U.S. Pat. No. 5,306,492, also in the name of the same applicant, discloses oligosaccharide conjugate vaccines and an improved method for producing said oligosaccharide-based conjugate vaccines. The method involved the activation of the oligosaccharide haptens at high temperature and at the discovered end-reducing group before being covalently coupled to the carrier protein via a linker molecule; a typical conjugate expressed bivalent specificity (to the Protein CRM197 and to the type (or group)-Ps); it used mono-functional oligosaccharides; the molecular construct induced serological specificity to the carrier protein and to the single-carried carbohydrate structure.

EP 1501542 in the name of the same applicant discloses a new method of producing HMW poly-disperse, cross-linked, polysaccharide-based conjugate antigens in high yield; a typical conjugate expressed specificity to the protein tetanus toxoid and to the carried type (or group)-Ps; it used poly-functional polysaccharides coupled to poly-functional protein carriers; the molecular construct induced serological specificity to the carrier protein and to the single-carried carbohydrate structure.

In addition, Porro M. et al. in *Medecine Tropicale*, 43: 129-132, 1983 first introduced the activation chemistry of a meningococcal group B oligosaccharide (previously hydrolyzed in controlled acidic conditions) at its end-reducing group, by ammonia and via reductive amination at low temperature (25-37° C.); such mono-functional amino-group bearing oligosaccharide was then activated by the bis-succinimidyl ester of adipic acid and then conjugated to the amino groups of the Lysine residues of the carrier protein CRM197. The activated oligosaccharide antigen was mono-functional in the conjugation process and conjugation occurred without the previous activation of the carrier protein CRM197. Moreover, Porro M. et al. in *Molecular Immunology*, 22: 907-919 (1985) first disclosed the activation chemistry of a pneumococcal type 6A oligosaccharide (previously hydrolyzed in controlled acidic conditions) at its end-reducing group, by ammonia and via reductive amination in their paper titled "Specific antibodies to diphtheria toxin and type 6A pneumococcal capsular polysaccharide induced by a model of semi-synthetic glycoconjugate antigen". Such mono-functional amino-group bearing oligosaccharide was then activated by the bis-succinimidyl ester of adipic acid and then conjugated to the amino groups of the Lysine residues of the carrier protein CRM197. The activated oligosaccharide antigen was mono-functional in the conjugation process and without the previous activation of the carrier protein.

In a later paper in Molecular Immunology, 23: 385-391, (1986), the same authors featured a two-steps conjugation process to the same protein carrier CRM197, of two capsular oligosaccharides (derived from a Gram-negative and a Gram-positive bacterium, respectively) using the activation chemistry and the conjugation chemistry disclosed in the previous papers cited. Both the activated oligosaccharide antigens were mono-functional in the conjugation process and without the previous activation of the carrier protein. It is observed that the conjugate disclosed in such paper involves different end-point activated low MW capsular oligosaccharides (namely Ps of *Streptococcus pneumoniae* type 6A and Ps group C of *Neisseria meningitidis*). The use of such end-point activation provides low coupling yields therefore resulting in a disproportioned, huge, amount of carrier protein with respect to the maximum amount of the two carried oligosaccharide structures (around 31.2 µg of CRM197 with 4.8 µg of Ps 6A and 3 µg of Ps type C, see page 387, left column of the above referred 1986 paper). Finally, in a later paper (Porro M. Edited by R. Bell and G. Torrigiani (World Health Organization), pages 279-306; John Wiley & Sons Publishers, New York 1987, the author of the present invention summarizes the concepts and the technical procedures above referenced for conjugate antigens composed of protein carrier and a maximum of two different carbohydrate structures. In developing the above state of the art, the preferred (not limitative) embodiment of the basic molecular construct subject of the present invention is composed by a multivalent, preferably a tetra-valent semisynthetic glycoprotein which features built-in multiple epitopes and expresses its helper T-dependent immunogenic specificity "in vivo" to the protein CRM197, as well as to three carried type-specific Ps, for example Ps of *S. pneumoniae*. As an example, any triad of the Ps type 1, 2, 3, 4, 5, 6A, 6B, 6C, 7F, 8, 9N, 9V, 10A, 11A, 12F, 14, 15B, 17F, 18C, 19A, 19F, 20, 22F, 23F, 33F of *S. pneumoniae* such as the triad consisting of the Ps type 3, 6A, 7F may be conjugated to the carrier protein. As an example, the term tetra-valent is referred the carrier protein antigen (acting per se as an antigen and not merely as a carrier) plus the three carried Ps antigens.

Thus, the novel new molecular construct induces serological specificity to the carrier protein and to each of the three carried carbohydrate structures.

This semi-synthetic tetravalent antigen can be considered as the novel new precursor of a new generation of conjugate antigens expressing multiple specificities for obtaining vaccines with an always broader spectrum of protection against a variety of bacterial pathogens while drastically reducing the amount of carrier protein, in order to obtain a rational improvement on:

A) the cost of production of the vaccines;

B) their production efficiency in terms of improvement of coupling yield that allowed the synthesis of the glycoprotein with three (or more) Ps antigens (also featuring high MW);

C) their production accuracy in terms of quantitative determination from the serological point of view of the amount of covalently bound Ps by using the specific inhibition-ELISA assay reported in the present application, for an accurate quantification of the multiple carbohydrate antigens present in the disclosed molecular construct, on the basis of immunochemical, rather than chemical quantification of the cited prior art (see Porro et al. 1986), especially in the various cases where highly significant similarities exist among specie-specific carbohydrate structures;

D) their safety as related to the lower amount of the protein dosage impacting on the immune system of the target population. In fact, said protein dosage is ca.30% (around 10 µg of protein in the dose involving a whole 15-valent formulation at 2 µg protein/triad/dose) of the protein dose present in the conjugate of CRM197 with the two Ps of the paper Porro et al., 1986. Such reduction would not be predictable for the skilled person in such amount based on the available stoichiometry reported in the paper where an immunizing dose would contain at least 31.2 µg of CRM197; therefore, for a multivalent composition comprising 13 or 15 conjugated antigens, even assuming the possibility of preparing, according to the previous chemistry, the multiple tetravalent molecular model detailed of the invention, the amount of protein CRM197 in the formulation would be 31.2×15/3=156.0 µg vs. 10 µg of the multivalent conjugate of the invention; and, consequently:

E) the public utility of such conjugate vaccines.

The present invention opens new avenues in the field of clinical immunology and vaccinology. In fact, the built-in multiple antigenicity of the disclosed molecular construct, specific for different bacterial antigens, actually parallels, in the innovative field of poly-pharmacology, the synthesis of a drug designed a priori for simultaneously reaching multiple receptors of pharmacological relevance, so allowing the reduction of the number of drugs to be administered in associated form (Besnard J. et al., Nature, 492: 215-220, 2012). Therefore, it is an object of the present invention an antigenic multivalent molecular construct consisting of a basic unit comprising a helper-T dependent carrier protein covalently bound to a minimum of three carbohydrate structures of different serological specificity, wherein each carbohydrate structure comprises at least one of the repeating basic antigenic epitope consisting of a minimum of five to twelve monosaccharide residues, preferably a minimum of eight to twelve monosaccharide residues, as assessed by molecular mass determination and NMR spectroscopy (equivalent to different numbers of Basic Repeating Units depending from homologous or heterologous sequences), said repeating basic antigenic epitopes being assessed by reactivity with type-specific or group-specific polyclonal or monoclonal antibodies through the determination of their respective $MIC_H$ values in the inhibition of their homologous Polysaccharide-Antibody reference system. According to the present invention, the term carbohydrate structures is intended to comprise oligosaccharides (natural or synthetic) or polysaccharides (such as capsular polysaccharides).

The T-helper dependent carrier protein of the antigenic multivalent molecular construct according to the invention is covalently bound to a minimum of three (for example three or four or five) carbohydrate structures of different serological specificity up to the limit of reactivity of the nucleophylic amino groups of the structural amino acids, mainly Lys but also, for example, of the basic features of Arg and Hys, present in the carrier protein structure involved in the coupling reaction.

According to preferred embodiments of the present invention the helper-T dependent carrier protein covalently bound to a minimum of three different carbohydrate structures of different serological specificity, is selected between the group of natural diphtheria mutant protein CRM197 (PRF 1007216A), diphtheria toxoid (CAE11230.1 of the homologous toxin), tetanus toxoid (ID NO. AAK72964.2 of the homologous toxin), Protein D from *Haemophilus influenzae* (AAA24998.1); pneumococcal surface proteins (PspA EMBL CBW33751.1 and PspC EMBL ACF56456.1); pneumococcal toxin (Pneumolysin EMBL ACF56060.1) or variants and derivatives thereof. Particularly, when the tetanus toxoid is employed it is preferred to employ a chemically derivatized toxoid by adipic acid dihydrazide spacer (tetanus toxoid-ADH). According to the most preferred embodiment of the present invention the carrier protein is the natural diphtheria mutant protein CRM197.

Such protein was first reported by Uchida and Pappenheimer in the mid of the seventy's (Uchida T. et al., J. Biol. Chem. 248, 3838-3844, 1973) and its possible use as novel immunogen against diphtheria toxin, as being in immunogenic correlation with diphtheria toxoid, was already reported by the applicant (Porro M. et al., J. Infect. Dis., 142 (5), 716-724, 1980). Since then, the applicant used CRM197 as ideal helper-T dependent carrier protein for carbohydrate antigens, once it became understood the reasons for the peculiar immunogenic characteristics of the latter group of antigens in human subjects, in the specific age involving the maturation of the immune system (from ca. 2 months to around 2 years of age). The protein CRM197 is composed by a sequence of 535 amino acids, just like diphtheria toxin (Giannini G. et al., Nucl. Acid Res., 12, 4063-4069, 1984) but shows a point-mutation at the amino acid in position 52, where Glu replaces Gly. Its antigenicity has been reported as mainly directed to four areas of the sequence, when using monoclonal antibodies, namely the AA sequences 1-156, 157-193, 293-345 and 465-535 (Zucker D. and Murphy J. R., Mol. Immunol. 21, 785-793, 1984). The protein also features 39 Lys residues and one amino terminal group, for a total of reactive 40 amino groups, which are purposely used for the chemical reactions involved in the various conjugation strategies.

The carrier protein CRM197 of the conjugate of the invention is usually prepared using the clones of *C. diphtheriae* $C7(\beta 197)^{tox-}$ but it may also be obtained by clones of *P. fluorescens*, among others.

According to preferred embodiments of the antigenic multivalent molecular construct of the invention the carried carbohydrate structures are selected among, but not limited to, Ps of *Streptococcus pneumoniae* (type 1, 2, 3, 4, 5, 6A, 6B, 6C, 6D, 7F, 8, 9N, 9V, 10A, 11A, 11B, 11C, 11F, 12F, 14, 15A, 15B, 15C, 17F, 18C, 19A, 19F, 20, 22F, 23A, 23F, 33F, 35B, among Ps of *Neisseria meningitidis* (group A,C, W135 and Y), *Haemophilus influenzae* (type b), *Mycobacterium tuberculosis* and *Klebsiella pneumoniae* (i.e. K1-K20 antigens), *Salmonella typhi* (type Vi), *Escherichia Coli* (type K1), *Vibrio cholerae* or a combination thereof. Preferably, such combination of Ps is carried out among Ps belonging to one or more infectious agent causing systemic and pulmonary diseases (*Streptococcus pneumoniae, Neisseria meningitidis, Haemophilus influenza, Mycobacterium tuberculosis, Staphylococcus aureus* and *Klebsiella pneumoniae*) in addition to Ps belonging to one or more infectious agents causing intestinal diseases (*Salmonella typhi* (type Vi), *Escherichia coli* (type K1), *Vibrio cholerae*) or Ps belonging to other infectious agents like *Candida albicans* causing systemic and genitourinary infections.

Based on the above embodiments, it is also possible to prepare hybrid molecular constructs where the carrier protein works as helper T-dependent vector for antigens of *S. pneumoniae* and *N. meningitidis* and other antigens simultaneously. These hybrid molecular constructs do not exist in nature as the antigenic surface of Gram-negative and Gram-positive bacteria differ significantly between them in terms of molecular architecture of the bacterial cell and the biologic mechanisms through which they induce protective immunity in mammalian hosts. For instance, while protective immunity induced against the capsular Ps of the Gram-negative bacterium *N. meningitidis* involves complement-dependent bactericidal activity, that induced by the Gram-positive bacterium *S. pneumoniae* involves opsono-phagocytic activity, yet complement-dependent. In the case of such a hybrid category of synthetic antigens both pathways are specifically induced (Porro M. et al., Molecular Immunol., 23: 385-391 (1986), a fundamental difference shown from the properties of each single natural antigens.

The present invention contemplates also the association of the antigenic multivalent molecular construct according to the invention with the class of LPS-based vaccines defined as Endotoxoids. Endotoxoids are nontoxic complexes of LPS with SAEP (Synthetic Anti Endotoxin Peptides) which have been shown to be useful in administering LPS as immunogen to mammalians (Rustici A. et al., Science, 259:361-365, 1993).

Such association may contemplate the separate, simultaneous or sequential use or administration of the antigenic multivalent molecular construct and the Endotoxoid(s) of gram negative bacteria. The Endotoxoid may be selected among Endotoxoid B (*N. meningitidis* Group B), Endotoxoid of *E. coli, S. typhi, V. cholerae, S. enteritidis, B. pertussis*.

Hybrid molecules according to the described molecular construct may also include the capsular polysaccharide of *Mycobacterium tuberculosis*, a pathogen which is continuously expanding throughout the world and for which a "sterilizing" vaccine, that is a vaccine which is protective in the bloodstream and in the lungs of the host, still does not exist. The polysaccharide capsule of *M. tuberculosis* predominantly consists of an α-D-(1→4)-glucan polymer with α-(1→6) branches which displays structural similarities with cytosolic glycogen. Mycobacterial α-glucan has an apparent molecular mass of $1.3 \times 10^7$ and is expressed both in vitro and in vivo (Schwebach, J. R., et al. 2002. Infect. Immun. 70:2566-2575); also, accompanying antigens like the glycolipids LAM (Lipoarabinomannan) and PIM (phosphatidylinositol mannoside) are possibly associated with the polysaccharide capsule. One or all of these carbohydrate antigens present in the capsular layer may then be conjugated to a carrier protein like CRM197, as an example, and to become part of the molecular construct of the invention.

It is also possible to foresee an antigenic multivalent molecular construct wherein the carried carbohydrate structures are those belonging to *Mycobacterium bovis* for the prevention of the infection affecting, other than humans, cattle, pigs, domestic cats, equids or sheep cattle.

Another case where the multivalent molecular construct of the invention can be applied with substantial advantages in terms of having a rational formulation design for a new vaccine, is that related to the pathogenic features of the fungus *Candida albicans*. The commensal fungus *Candida albicans* causes mucosal candidiasis in immunocompromised patients, which includes oropharyngeal, esophageal, gastrointestinal, and vaginal infections. Vulvovaginal candidiasis (VVC) and antimycotic-refractory recurrent VVC is also a frequent problem in healthy childbearing women. Both these mucosal infections can affect the quality of life and finding a new vaccine against candidal infections would be a new important tool to prevent mucosal candidiasis and would be of benefit to many patients. An effective systemic and local vaccine still does not exist in the prevention of such chronic, recurrent, infections. The antigenic repertoire of *C. albicans* contains, among others, several antigens of glucidic nature, namely the 1,3-β-glucan (Bromuro et al., 2010), and the L-mannans as β-1,2-mannotriose (Han et al., 2010; Xin et al., 2008). Such structurally different carbohydrate antigens can be all conjugated to a carrier protein of choice for preparing a multivalent entity like the one here disclosed, which to some extent can mimic the whole, carbohydrate-based, antigenic structure of the pathogen, which, in the case of genitourinary infections, may be also rationally associated with *E. coli* carbohydrate-based antigens in conjugated form.

Furthermore, another case where the multivalent molecular construct of the invention can be applied with substantial advantages in terms of having a rational formulation design for a new vaccine, is that related to the pathogenic features of *Staphylococcus aureus*. This pathogen, as reported by O'Riordan and Lee Olin. Microbiol. Rev., 17:218-234, 2004 and below synthesized, is an opportunistic bacterial pathogen responsible for a diverse spectrum of human and animal diseases. *Staphylococcus* is also a major cause of wound infections and has the invasive potential to induce osteomyelitis, endocarditis, and bacteremia, leading to secondary infections in any of the major organ systems. Staphylococcal infections occur most frequently when the skin or mucosal barriers are breached, following insertion of a foreign body, and in hosts with compromised immune systems. Because of the prevalence of antibiotic-resistant strains and the recent emergence of clinical isolates resistant to vancomycin, control of *S. aureus* has become increasingly difficult. *Staphylococcus* plays a major role in nosocomial infections and recently has been acknowledged as an important cause of community-acquired infections. Community acquired *S. aureus* infections often occur in otherwise healthy individuals who lack the expected risk factors for *S. aureus* infections, e.g., recent hospitalization or surgery, residence in a long-term-care facility, or use of injected drugs. Among other antigens, the bacterial component that mainly affect the pathogenesis of *S. aureus* infections include a capsular polysaccharide, which allows staphylococci to adhere to eukaryotic membranes, resist opsonophagocytosis, lyse eukaryotic cells, and trigger the production of a cascade of host immunomodulating molecules. Capsules from at least 18 *S. aureus* strains have been described and at least four of them characterized. Each contains hexosaminuronic acids. Biochemical characterizations have been performed on some polysaccharides purified. Strain M expresses a type 1 capsule with the following structure: $(\rightarrow 4)$-α-d-GalNAcA-$(1 \rightarrow 4)$-α-d-GalNAcA-$(1 \rightarrow 3)$-α-d-FucNAc-$(1 \rightarrow)_n$; a taurine residue is amide linked to every fourth d-GalNAcA residue. Two other strains, D and SA1 mucoid, produce capsules that are serologically and biochemically similar to that produced by strain M. The capsule of serotype 2 has the structure:$(\rightarrow 4)$-β-α-G1cNAcA-$(1 \rightarrow 4)$-β-dGlcNAcA-$(1$-alanyl)-$(1 \rightarrow)_n$. Type 5 and 8 capsular polysaccharides (CP5 and CP8, respectively) are structurally very similar to each other and to the capsule made by strain T. Type 5 has the structure $(\rightarrow 4)$-3-O-Ac-β-α-MβηNAoA-$(1 \rightarrow 4)$-1-FucNAc-$(1 \rightarrow 3)$-β-d-Fuc NAC-$(1 \rightarrow)_n$, and type 8 has the structure $(\rightarrow 3)$-4-O-Ao-β-d-ManNAcA-$(1 \rightarrow 3)$-α-1-FucNAc-$(1 \rightarrow 3)$-β-d-FucNAc-$(1 \rightarrow)_n$. Type 5 and 8 polysaccharides differ only in the linkages between the sugars and in the sites of O-acetylation of the mannosaminuronic acid residues, yet they are serologically distinct.

Very recently (Nanra et al., Human Vaccines and Immunotherapeutics, 9:3, 480-487, 2013) has been reported the role of the capsular Ps of *S. aureus* in preventing the non-specific OPA (opsonophagocytosis) killing in the presence of variable amount of complement but in the absence of specific antibodies to Ps; in contrast, when in the presence of specific antibodies to Ps raised in rhesus macaques by CRM197-Ps conjugates of type 5 and 8, OPA killing was very efficient on *S. aureus*, underlining the fundamental role of the antibodies to the Ps capsule for eliciting the immunological defenses to this pathogen when in capsulated form.

Accordingly, it is also the subject of the present application the innovative formulation of a vaccine against *S. aureus*, composed of a molecular construct in the form of glycoconjugate carrying at least three different type-specific Ps antigens of *S. aureus* on the carrier protein of choice, most preferably CRM197.

According to one preferred embodiment the carried carbohydrate structures of *S. pneumoniae* antigens selected according to a specific embodiment of the invention are the polysaccharide type 3, 6A, 7F.

The polysaccharide type 3 responds to the following structure (Reeves R. E. and Goebels W. F., J. Biol. Chem., 139: 511-519, 1941):

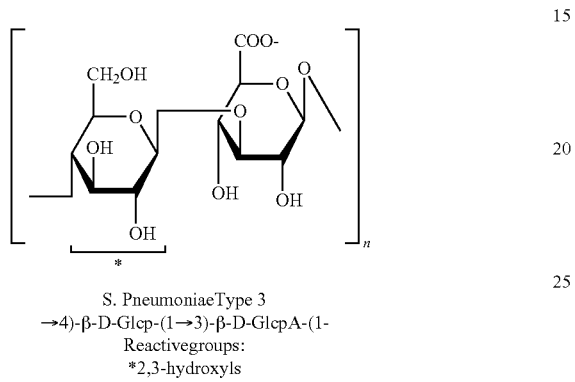

S. PneumoniaeType 3
→4)-β-D-Glcp-(1→3)-β-D-GlcpA-(1-
Reactivegroups:
*2,3-hydroxyls The structure features one pair of —OH groups/Base Repeating Unit (BRU) which means there is a possibility to activate it at various degrees using the method disclosed by the Applicant in the above mentioned Patent EP 1501542.

The polysaccharide type 6A responds to the following structure (Rebers P. A. and Heidelberger M., J. Am. Chem. Soc., 83: 3056-3059, 1961):

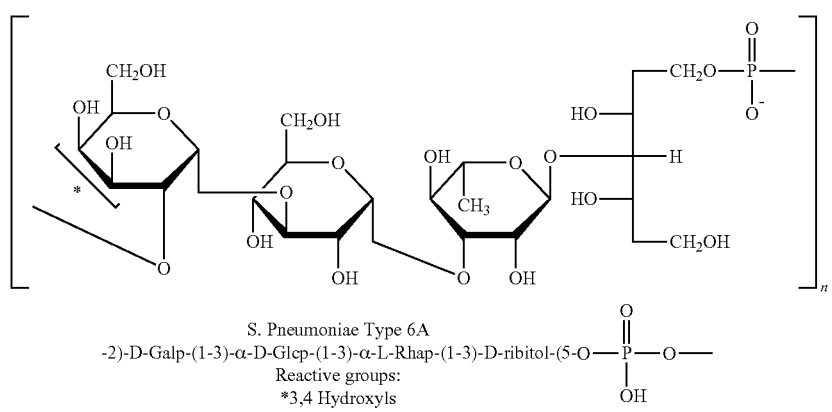

S. Pneumoniae Type 6A
-2)-D-Galp-(1-3)-α-D-Glcp-(1-3)-α-L-Rhap-(1-3)-D-ribitol-(5-O—P—O—
Reactive groups:
*3,4 Hydroxyls The structure features one pair of —OH groups/Base Repeating Unit (BRU) which means there is a large possibility to activate it at various degrees using the method disclosed by the applicant in EP 1501542.

The polysaccharide type 7F responds to the following structure (Moreau M. et al., Carbohydrate Res., 182 (1): 79-99, 1988):

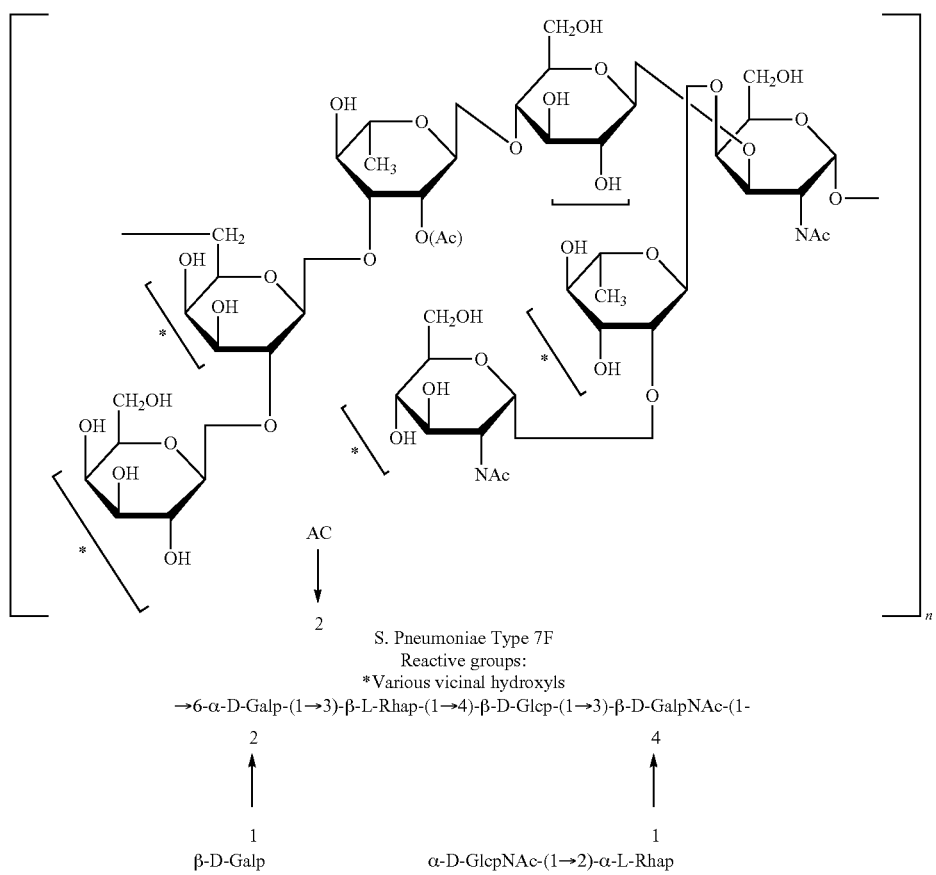

S. Pneumoniae Type 7F
Reactive groups:
*Various vicinal hydroxyls
→6-α-D-Galp-(1→3)-β-L-Rhap-(1→4)-β-D-Glcp-(1→3)-β-D-GalpNAc-(1-
                                                2                         4
                                                ↑                         ↑
                                                1                         1
                                            β-D-Galp              α-D-GlcpNAc-(1→2)-α-L-Rhap The structure features well five pairs of —OH groups/Base Repeating Unit (BRU) which means there is a huge possibility to activate it at various degrees using the method disclosed in EP 1501542.

Other possible multivalent conjugates (in addition or in alternative to CRM197-3, 6A, 7F) where the protein CRM197 (or any other immunogenic protein) serves as helper T-dependent carrier of S. pneumoniae polysaccharides are selected between the following non limitative configuration of triads:

CRM197-4,5,9V; CRM197-1,6B,14; CRM197-18C,19A, 23F; CRM197-6C,19F,22F; CRM197-12F,15B,33F.

It goes without saying that any combination (triad or quartet or more) of the Ps type 1, 2, 3, 4, 5, 6A, 6B, 6C, 7F, 8, 9N, 9V, 10A, 11A, 12F, 14, 15B, 17F, 18C, 19A, 19F, 20, 22F, 23F, 33F of S. pneumoniae may be contemplated.

According to another exemplificative embodiment the multivalent conjugates of the invention may contemplate the following triads of Ps: CRM197-3,6A,7F; CRM197-5,9V, 19F; CRM197-1,14,19A; CRM197-22F,23F,33F; CRM197-4,6B,18C.

The antigenic multivalent molecular construct of the invention may be either in monomeric or polymeric form. The invention is also directed to one or more than one antigenic multivalent molecular construct as above defined in a vaccine for the protection of a subject (preferably belonging to the human paediatric population) from the infections due to at least one agent selected among S. pneumoniae, N. meningitidis, H. influenzae, K. pneumoniae, M. tuberculosis, S. typhi, S. aureus and E. coli. Preferably, the combination of the antigenic multivalent molecular construct of the invention will be carried out by selecting antigenic multivalent molecular construct carrying Ps belonging to one or more infectious agent causing systemic and pulmonary diseases (such as Streptococcus pneumoniae, Neisseria meningitidis, Haemophilus influenzae, Mycobacterium tuberculosis, Staphylococcus aureus and Klebsiella pneumoniae) in addition to Ps belonging to one or more infectious agent causing intestinal diseases (Salmonella typhi (type Vi), Escherichia Coli (type K1, V. cholerae) or Ps originating from other infectious agents like the commensal fungus Candida albicans causing genitourinary infections also in association with the pathogen E. coli.

It is in fact possible to foresee a vaccine against Candida albicans and Escherichia coli infections (preferably for the immunization of the female population) comprising one or more antigenic multivalent molecular construct wherein the carried carbohydrate structures are those belonging to Candida albicans and Escherichia coli.

Another aspect of the present invention contemplates a vaccine against Mycobacterium bovis infections for the immunization of cattle, pigs, domestic cats, equids or sheep-cattle.

Furthermore, the invention features a vaccine formulation comprising one or more molecular constructs of different antigenic specificities according to the present invention, in a physiologically acceptable vehicle, optionally together with an adjuvant and/or excipients pharmaceutically acceptable.

The invention is further directed to a broad-spectrum polyvalent vaccine formulation as above defined, for use in human medical field for the protection of a subject from the infections due to at least one agent selected among *S. pneumoniae, N. meningitidis, H. influenzae, K. pneumoniae, S. aureus, M. tuberculosis, S. typhi, E. coli, V. cholerae* and *C. albicans*. Preferably, said subject belongs to the paediatric population.

In addition, the molecular model disclosed in the present application is the base for a broad-spectrum polyvalent vaccine for the prevention of type-specific *S. pneumoniae* bacterial infections containing from a minimum of 7 types (for example 9, 12, 15, 18, 21, 24) and up-to 25 different carbohydrate structures of type I, 2, 3, 4, 5, 6A, 6B, 6C, 7F, 8, 9N, 9V, 10A, 11A, 12F, 14, 15B, 17F, 18 C, 19A, 19F, 20, 22F, 23F, 33F.

It is also possible to foresee a vaccine contemplating the combination of one or more tetravalent antigenic molecular construct (carrying three Ps) of the invention with one bivalent or trivalent antigenic construct (carrying one or two Ps) or alternatively with one pentavalent antigenic construct (carrying four Ps), when the final number of carbohydrate structures that the skilled person intends to achieve is different from a multiple of three.

When considering the basic conjugate carrying three moles (or fractions of it) of structurally different carbohydrate antigens per mole (or fractions of it) of carrier protein, the amount of carrier protein can be reduced to ca. 30% of that present in any of the today available pneumococcal conjugate formulations for the paediatric population (e.g.: Prevnar which is the object of the patent EP1868645, and Synflorix).

A practical example of broad-spectrum (e.g.:18-valent) formulation of a vaccine for the prevention of IPD (Invasive Pneumococcal Disease) due to *S. pneumoniae*, which is based on the antigenic multivalent molecular construct disclosed in this application, is the association of at least three, four, five or preferably all the following multivalent conjugates, where the protein CRM197 (or any other immunogenic protein) serves as helper T-dependent carrier:

CRM197-3,6A,7F; CRM197-4,5,9V; CRM197-1,6B,14; CRM197-18C,19A,23F; CRM197-6C,19F,22F; CRM197-12F,15B,33F.

In such an example, just six multivalent conjugates cover the broad-spectrum of serotypes selected.

In sharp contrast, nowadays available formulations would require the association of eighteen conjugates. It goes without saying that any combination (triad or quartet) of the Ps type 1, 2, 3, 4, 5, 6A, 6B, 6C, 7F, 8, 9N, 9V, 10A, 11A, 12F, 14, 15B, 17F, 18C, 19A, 19F, 20, 22F, 23F, 33F of *S. pneumoniae* may be contemplated. Another preferred example of broad-spectrum (e.g.: 15-valent) formulation of a vaccine for the prevention of IPD (Invasive Pneumococcal Disease) due to *S. pneumoniae*, comprises multivalent conjugates of the invention contemplating the following triads of Ps: CRM197-3,6A,7F; CRM197-5,9V,19F; CRM197-1,14,19A; CRM197-22F,23F,33F; CRM197-4,6B,18C.

The injected amount of protein carrier in the former formulation is therefore ca. 30% (on weight basis) of the amount of carrier protein present in the latter formulation, with a highly significant reduction of at least 70% of it (on weight basis).

To make a comparison, the total amount of carrier protein today present in the 13-valent "Prevnar" vaccine (formulation composed of 13-associated monovalent antigens, object of the patent EP 1868645) is ca.32 µg, at the clinical dose of ca. 2 µg Protein/ca. 2 µg of each Ps antigen conjugated, for a total of 31 µg of Ps antigens [average ratio (R) Protein/Ps (w/w)=1.03]; at about the same ratio Protein/type-specific Ps (as shown by the above disclosed multivalent conjugate CRM197-3,6A,7F), the total amount of carrier protein in the exemplified 18-valent formulation is just 12 µg or the 37.5% of that present in the 13-valent formulation of "Prevnar" (data on the composition of the "Prevnar" vaccine and "Synflorix" vaccine are from the publically available documents released from US-FDA and EMA).

Additional examples of vaccine formulations are based on the antigenic multivalent molecular construct according to the invention for the prevention of group-specific *N. meningitidis* bacterial infections (group A, C,W135,Y).

The same strategy relative to the conjugation process and controls above disclosed for the multivalent antigenic molecular construct of *S. pneumoniae* type 3, 6A and IF, can be used for other carbohydrate structures like those of *N. meningitidis*.

In this case, just one multivalent antigen containing the group-specific carbohydrate structures (polysaccharide A, C,W135 and Y) may constitute the formulation of the vaccine.

Therefore it is another object of the invention a broad spectrum vaccine formulation for the prevention of the infection due to *Neisseria meningitidis* comprising an antigenic multivalent molecular construct containing the group-specific carbohydrate structures A, C, W135 and Y.

According to a preferred embodiment the present invention is directed to a broad spectrum vaccine formulation for the prevention of the pulmonary infection (preferably in pediatric population) due to more than one infectious agent selected among *Streptococcus pneumoniae, Neisseria meningitidis, Haemophilus influenzae, Staphylococcus aureus, Klebsiella pneumoniae, M. tuberculosis*, comprising more than one antigenic multivalent molecular construct containing said agent-specific carbohydrate structures. Alternatively, the present invention relates to a broad spectrum vaccine formulation for the prevention of the intestinal infections (in the pediatric or adult human population) due to more than one infectious agent selected between *Salmonella typhi, Escherichia coli* and *Vibrio cholera*.

Another embodiment foresees a broad spectrum vaccine formulation for the prevention of the systemic or genitourinary infections due to pathogens like the commensal fungus *C. albicans* and *Escherichia coli*, said vaccine comprising more than one antigenic multivalent molecular construct containing said agent-specific carbohydrate structures.

According to a particular embodiment of the present invention the aforementioned vaccine formulations may be administered separately, simultaneously or sequentially with an Endotoxoid antigen of gram negative bacteria, said Endotoxoid being selected in the group consisting of Endotoxoid of *N. meningitidis* Group B, *E. coli, S. typhi, V. cholerae, S. enteritidis, B. pertussis*.

When considering the basic conjugate construct carrying the four structurally different carbohydrate antigens, the amount of carrier protein can be reduced to at least 25% of that present in any of the today available associated conjugate formulations (e.g.: "Menactra" and "Menveo") according to the public available documents on their composition and formulation (a total of 48 and 47 µg/dose of Diphtheria Toxoid and CRM197, respectively) released from US-FDA and EMA.

The immunogenic dose of polyvalent formulations of the molecular construct disclosed in this application is referred to the dose of each carbohydrate structure carried. In this respect, the dose may range between 0.1 to 10 µg, preferably 1 µg, of each conjugated carbohydrate antigen in infants and children. Those that are expert in the clinical field will help finding the optimal dose in the target population.

Preferably, said vaccine formulations further comprises a mineral or a chemically synthetic or a biological adjuvant. Mineral or chemically synthetic or biological adjuvants can be used with the molecular construct disclosed in this application, in order to benefit from any immunological boost that can be effective in lowering the optimal immunogenic dose in humans so to further reduce the total amount of carrier protein. Particularly, preferred inorganic adjuvants in the vaccine formulations according to the invention for use in human beings are selected between Aluminium Phosphate ($AlPO_9$) and Aluminium Hydroxide; preferred organic adjuvants are selected from squalene-based adjuvants such as MF59, QF 21, Addavax; preferred bacterial antigens are selected between Monophosphoryl-lipid A, Trehalose dicorynomycolate (Ribi's adjuvant). In vaccine formulations for use in the veterinary field Freund's adjuvant (complete or incomplete) is preferred. The dose of adjuvant may range between 0.1-1 mg/dose, preferably being 0.5 mg/dose.

More preferably, such formulation is suitable for the administration by subcutaneous or intramuscular or intradermal or transcutaneous route. Conveniently, such administration may be carried out by conventional syringe injection or needle-free tools.

The vaccine formulations according to the invention may be administered according to a protocol which requires single or multiple administrations, according to the physician, pediatrician or veterinary instructions.

The present invention is further directed to a conjugation process for preparing the antigenic multivalent molecular construct which employs the chemistry disclosed in the patent EP 1501542, where each of the at least three carbohydrate structures is chemically activated to mono-functionality or polyfunctionality by 0-de-hydrogen uncoupling via oxidation and reductive amination forming imine reduced bonds with an alkyl diamine spacer, then derivatized to active esters, such ester-derivative carbohydrate structures being finally and simultaneously coupled or step-by-step coupled to the amino groups of the polyfunctional carrier protein through the formation of amide bonds.

Preferably, said carbohydrate structures are chemically activated in their corresponding diamine butyric acid derivatives and the active esters are succinimidyl esters.

As an example, the chemical activation of the triad of polysaccharide type 3, 6A, 7F (or of the other preferred triad 4,5,9V; 1,6B,14; 18C,19A,23F; 6C,19F,22F; 12F,15B,33F; 5,9V,19F; 1,14,19A; 22F,23F,33F; 4,6B,18C) of *S. pneumoniae* to the homologous Ps-DAB (diamine butyric acid derivative) has been performed according to the process disclosed by the Applicant in claim 1 of EP 1501542, and the polyfunctional carrier protein was CRM197.

Alternatively, the conjugation process for preparing the antigenic multivalent molecular construct employs the chemistry disclosed in claim 8 of EP 1501542 involving simultaneous coupling or step-by-step coupling of the amino groups of the poly-functional carrier protein with the at least three different carbohydrate structures, via reductive amination forming imine-reduced bond, such carbohydrate structures being previously activated to monofunctionality or polyfunctionality, with or without spacers, by O-de-hydrogen uncoupling via oxidation. As it can be inferred, the above disclosed molecular model can be further developed to contain more than three (for example four or five) different carbohydrate structures per single mole (or fractions of it) of protein carrier, this possibility depending from three main parameters of the molecular construct:

a) the physical-chemical features of the carrier protein, which structure should feature the highest possible amount of Lysine residues (source of reactive —$NH_2$ groups);

b) the "ad hoc" selected polydisperse MW of the different carbohydrate structures featuring an optimal activation rate while limiting the negative effects of steric hindrance phenomena in the coupling reaction, and c) the efficiency of the chemistry used for the activation of the different carbohydrate structures and for the synthesis of the molecular construct (the preferred chemistry for a high efficiency in the optimal activation of carbohydrate structures is the O-de-hydrogen uncoupling via oxidation, with or without spacer, while that for a high efficiency in the conjugation reaction is through amide bond formation via active esters between the carbohydrate structures and the carrier protein; also preferred for the conjugation reaction, is the chemistry which uses the formation of an imine reduced bond between the O-de-hydrogen uncoupling oxidized carbohydrate structures, with or without spacers, and the carrier protein, via direct reductive amination).

The process of conjugation employed according to the invention foresees the multi-step activation of the (at least three) polysaccharides (that consequently may have indifferently, although homogeneously, either low or high MW) in order to improve the coupling yields with the carrier protein. This is different from the conjugation process of the prior art (see Porro et al. Molecular Immunology, Vol. 23, pages 385-391, 1986) involving the end-point activation at low temperature of the low MW Ps employed which, consequently, resulted in a low coupling yield while not involving the molecular cross-linking of the conjugate.

Another difference with the previous model lies in the stoichiometric features of that previous construct (w/w ratio Protein/Ps) as well as in the determination of the Ps employed which is carried out by immunochemistry in the present invention vs the chemistry approach used in the prior art. This has allowed the possibility in the present invention to determine the quantitative amount of Ps having very similar structures when present in the same molecular construct.

Finally, the present invention is directed to the antigenic multivalent molecular constructs which are obtainable through the conjugation processes above disclosed.

The present invention will be further illustrated according to preferred embodiments with particular reference to the enclosed figures, wherein.

Figure 1:
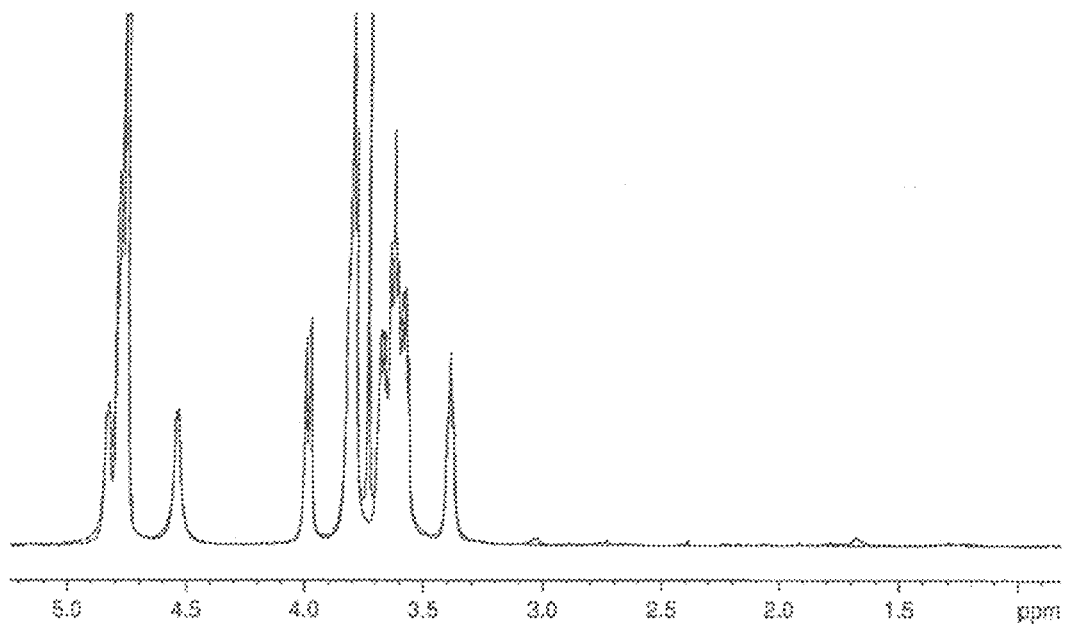
FIG. 1 shows a comparison between $^1$H-NMR spectrum of native Ps 3 (grey) and activated Ps 3-DAB 50% Ox (black) of Ps 3 and Ps3-DAB derivative.
Figure 2:
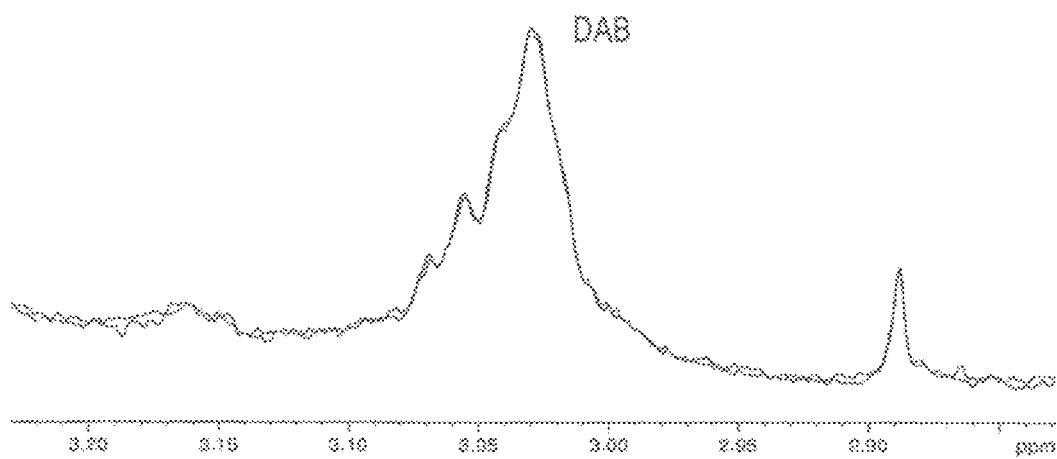
FIG. 2 shows $^1$H-NMR spectra of Ps 3-DAB 50% Ox, with diffusion filters. Spectrum in black 60% GRAD, spectrum in gray 2% GRAD assessing absence of free DAB in the derivative.
Figure 3:
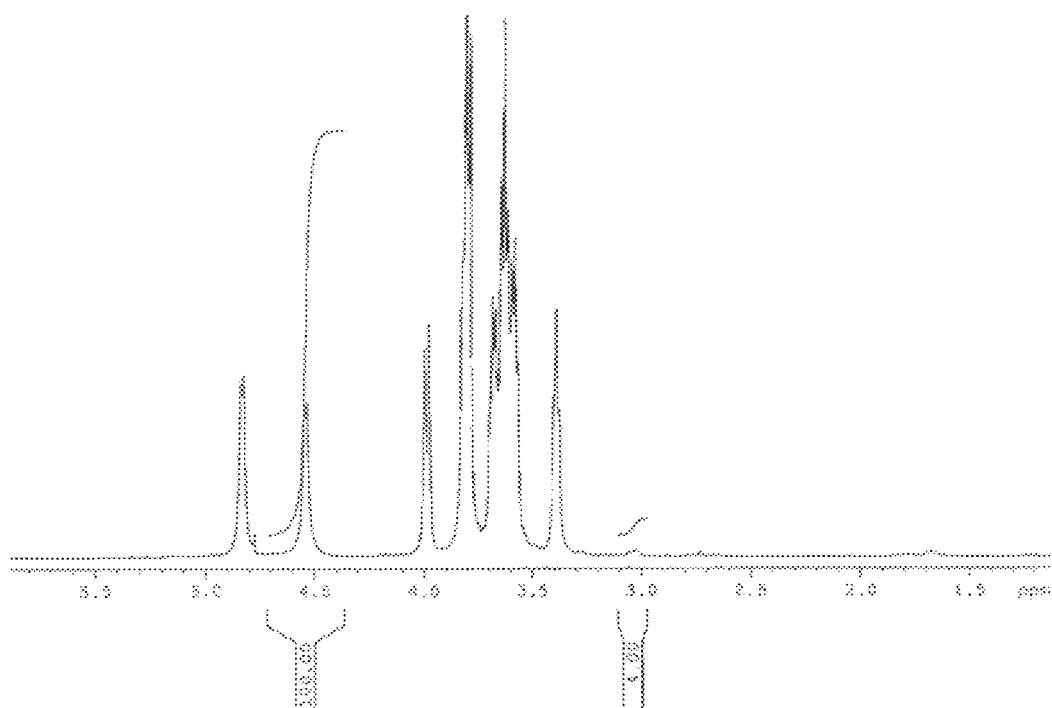
FIG. 3 shows Ps 3-DAB derivative, 50% Ox, $^1$H-NMR spectrum and quantization of DAB activation (2% on molar basis).
Figure 4:
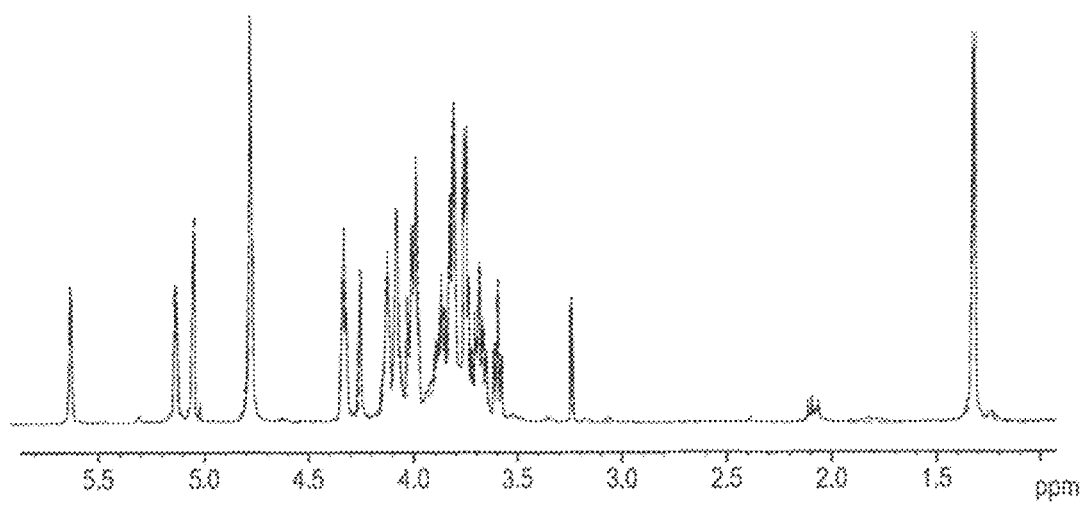
FIG. 4 shows a comparison between the $^1$H-NMR spectrum of native Ps6A (grey) and activated Ps6A-DAB derivative 50% Ox (black).
Figure 5:
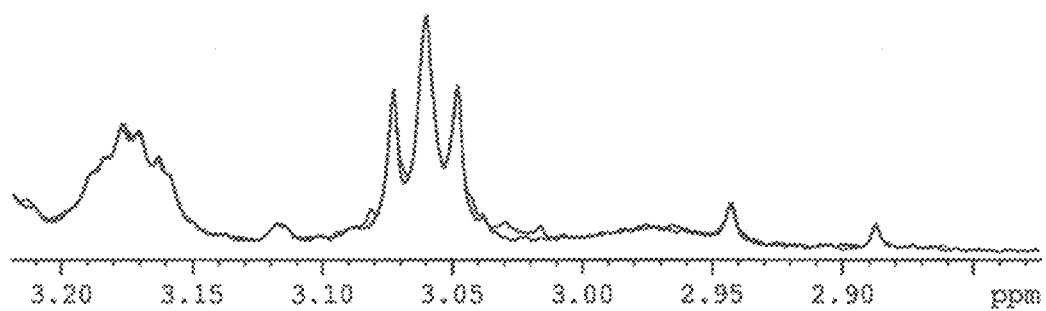
FIG. 5 shows $^1$H-NMR spectra of Ps 6A-DAB 50% Ox, with diffusion filters. Spectrum in black 60% GRAD, spectrum in gray 2% GRAD assessing absence of free DAB in the derivative.
Figure 6:
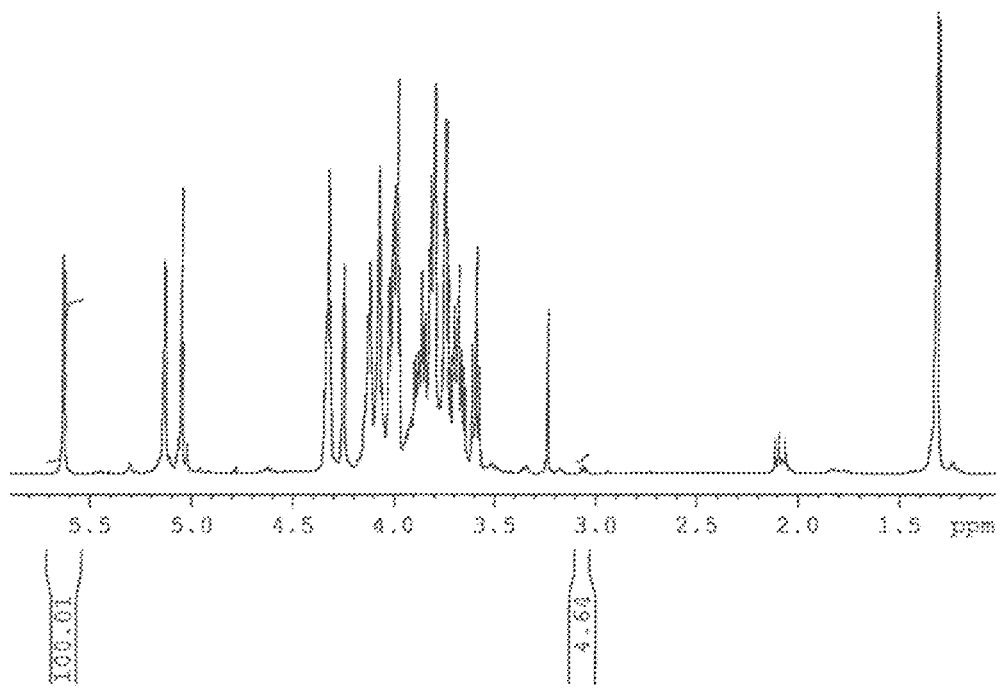
FIG. 6 shows Ps 6A-DAB derivative, 50% Ox, $^1$H-NMR spectrum and quantization of DAB activation (2.3% on molar basis).
Figure 7:
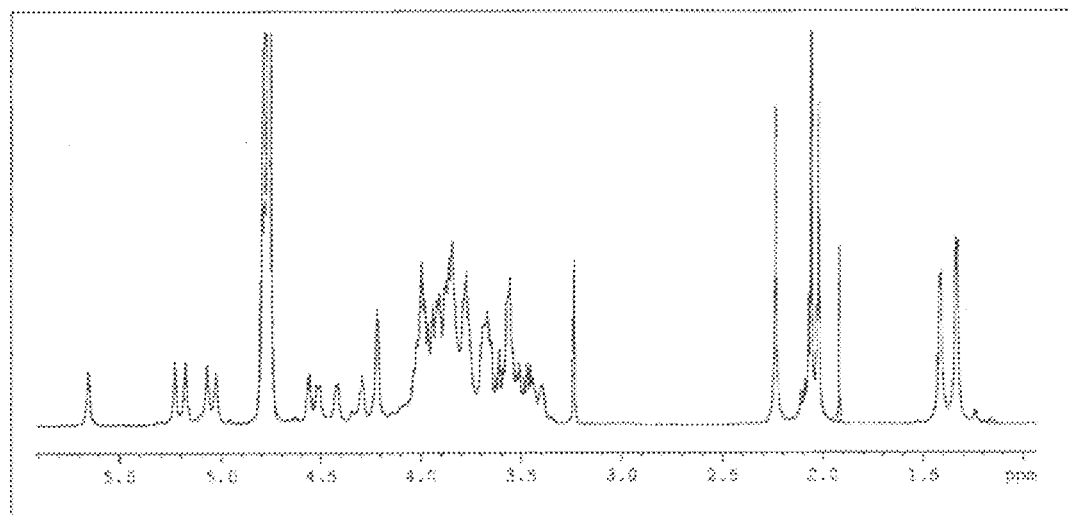

FIG. 7 shows a comparison between the $^1$H-NMR spectrum of native Ps7F (grey) and activated Ps7F-DAB derivative 10% Ox (black). The signal at 1.92 ppm, only present in the native Ps, is due to free acetate ion. OAc signal at 2.24 ppm remains the same after DAB activation.

Figure 8:
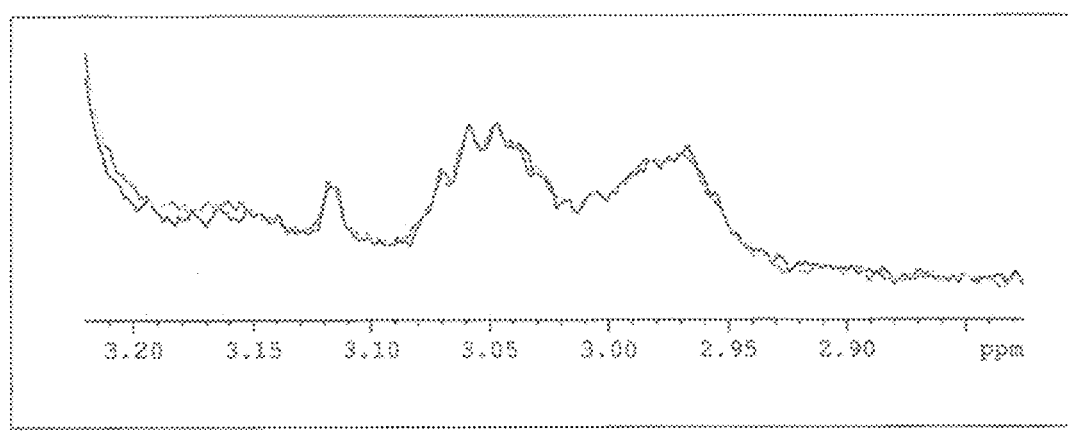

FIG. 8 shows $^1$H-NMR spectra of Ps 7F-DAB 10% Ox, with diffusion filters. Spectrum in black 60% GRAD, spectrum in gray 2% GRAD assessing absence of free DAB in the derivative.

Figure 9:
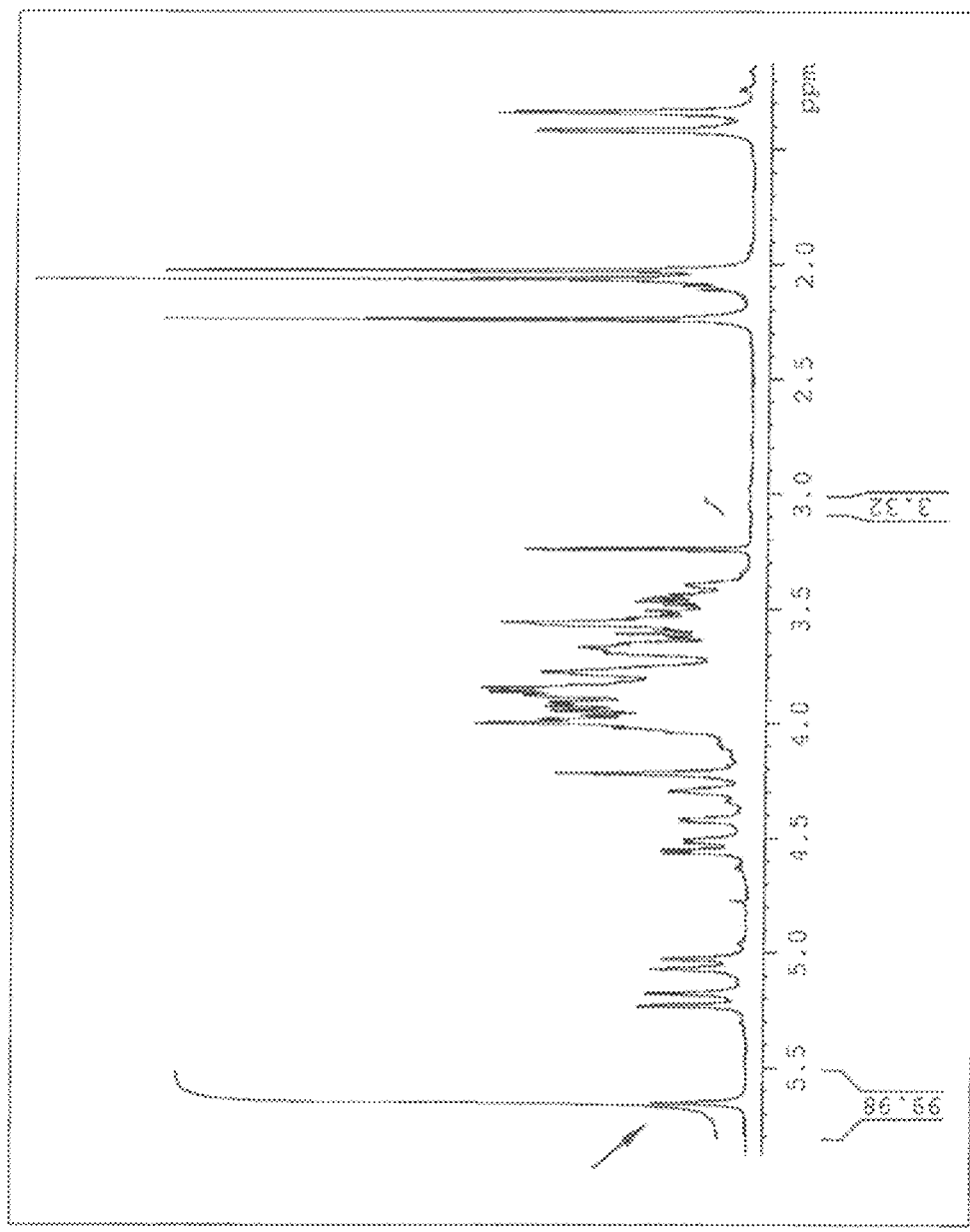

FIG. 9: shows Ps 7F-DAB derivative 10% Ox, $^1$H-NMR spectrum and quantization of DAB activation (1.7% on molar basis). Arrow indicates the reference signal at 5.65 ppm (α-proton of glucose or galactose) for quantization of the DAB activation.

Figure 10:
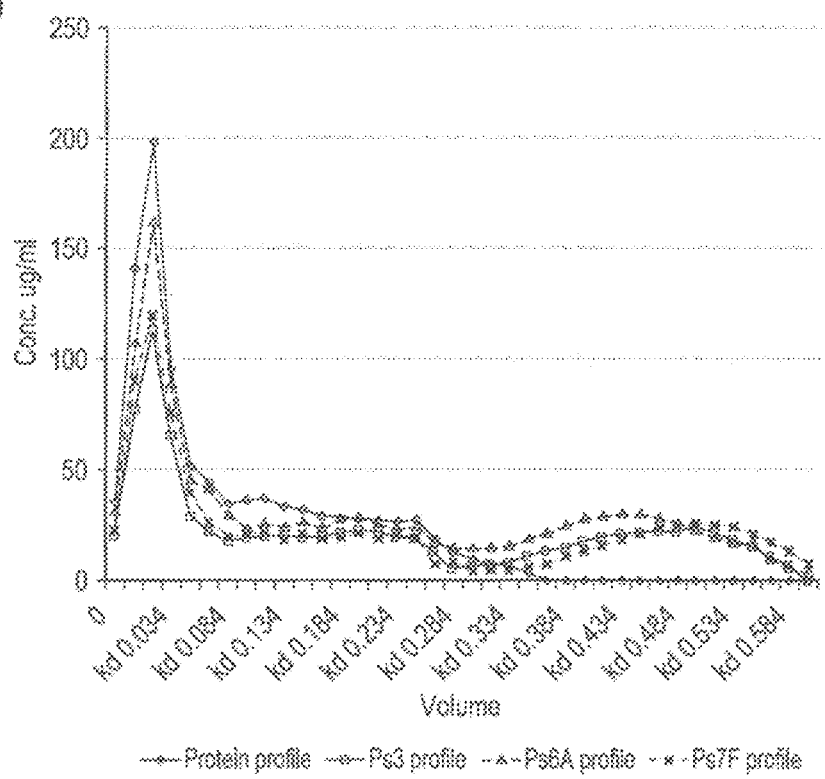

FIG. 10 shows GPC analysis of the antigenic multivalent molecular construct CRM197-3,6A,7F.

Figure 11:
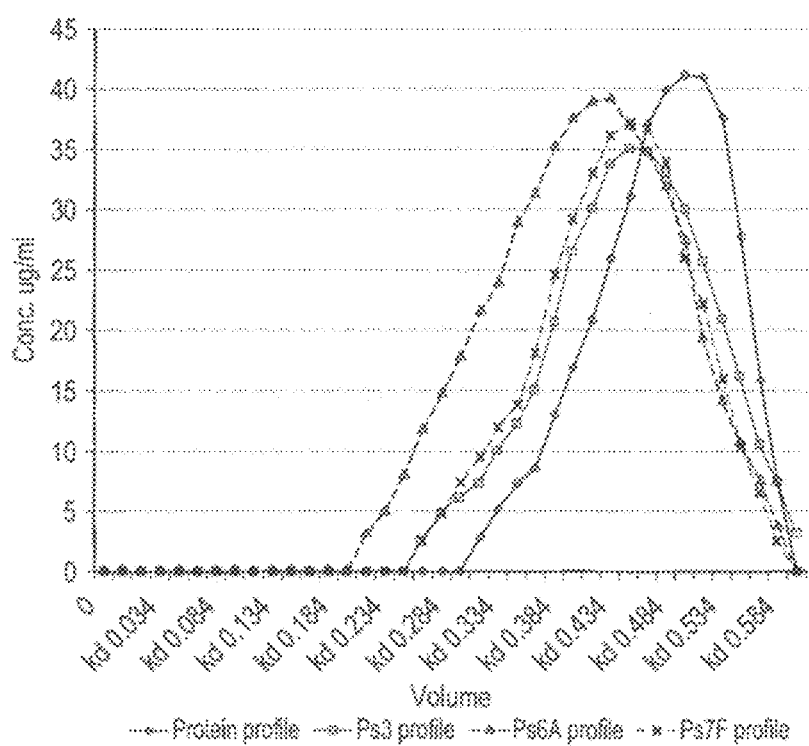

FIG. 11 shows the GPC analysis of the four components just mixed together (CRM197+Ps 3-DAB+Ps 6A-DAB+Ps 7F-DAB) in order to show absence of any significant amount of complex formation among the single antigens.

Figure 12:
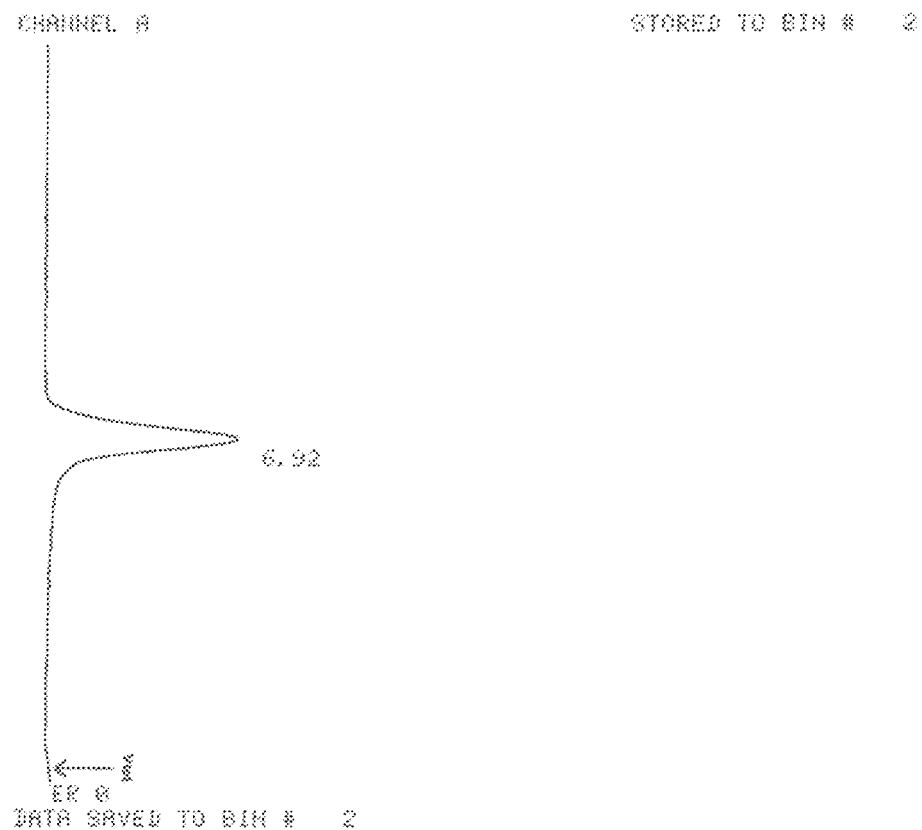

FIG. 12 shows SEC-HPLC analysis of the multivalent antigen, following purification on Sepharose 4B-CL, with specific reference to the profile of the carrier protein CRM197.

FIG. 13 shows SEC-HPLC analysis of CRM197 as native protein, when mixed with Ps 3-DAB, Ps 6A-DAB and Ps 7F-DAB.

FIG. 14 shows the SDS-PAGE analysis (9% Glycine buffer) showing the pattern of the purified multivalent antigen CRM197-3,6A,7F. Legend of the loaded samples: 1: CRM197 as reference; 2: Polydispersed MW of the purified multivalent conjugate antigen CRM197-3,6A,7F; 3: Mixture of CRM197+Ps3-DAB+Ps6A-DAB+Ps7F-DAB as reference.

FIG. 15 shows immunoblot analysis (Western-blot) of the multivalent antigen as qualitatively revealed by type-specific serum polyclonal antibody. Legend of the loaded samples: 1:
Multivalent conjugate CRM197-3,6A,7F (from line 2 of FIG. 14, above); 2: Mixture of CRM197+Ps3-DAB+Ps 6A-DAB+Ps7F-DAB as reference.

Figure 16:
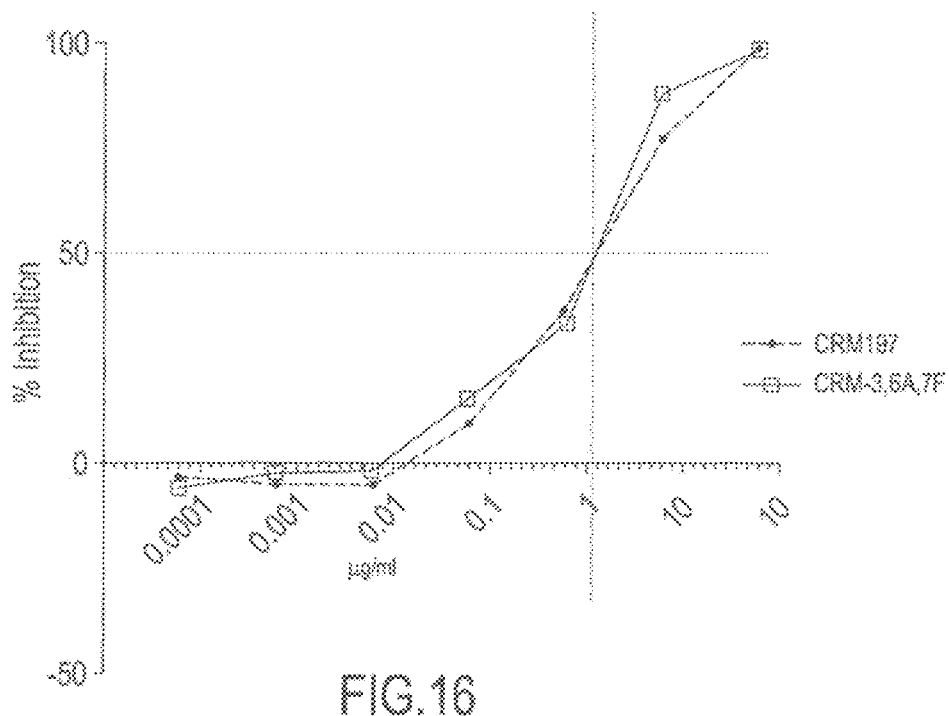

FIG. 16 shows the comparison between the % inhibition (expressed as MIC$_5$O for CRM197 native and in its conjugated form as CRM197-Ps,3,6A,7F.

Figure 17:
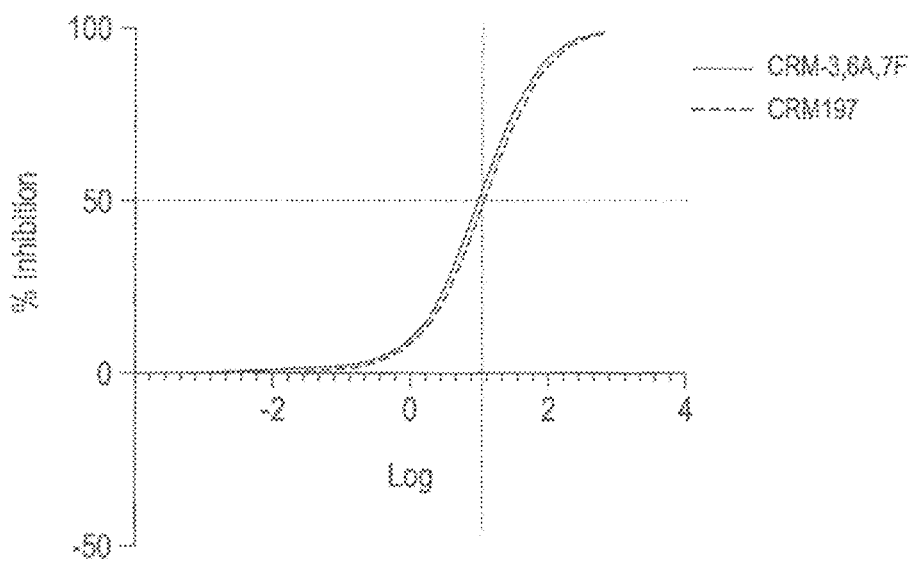

FIG. 17 shows the sigmoidal curve (log scale) referred to the graph of FIG. 16.

Figure 18:
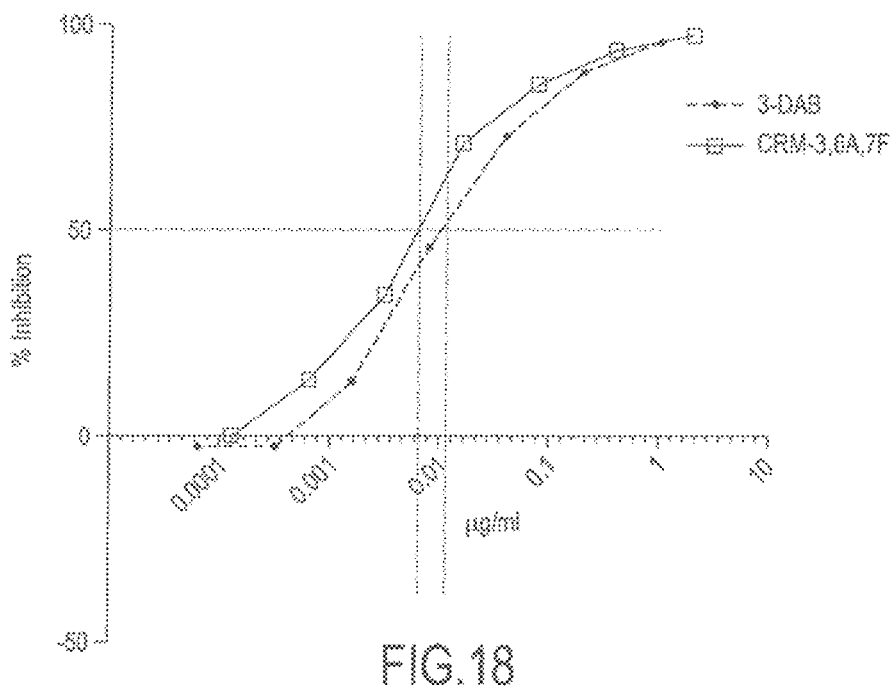
Figure 19:
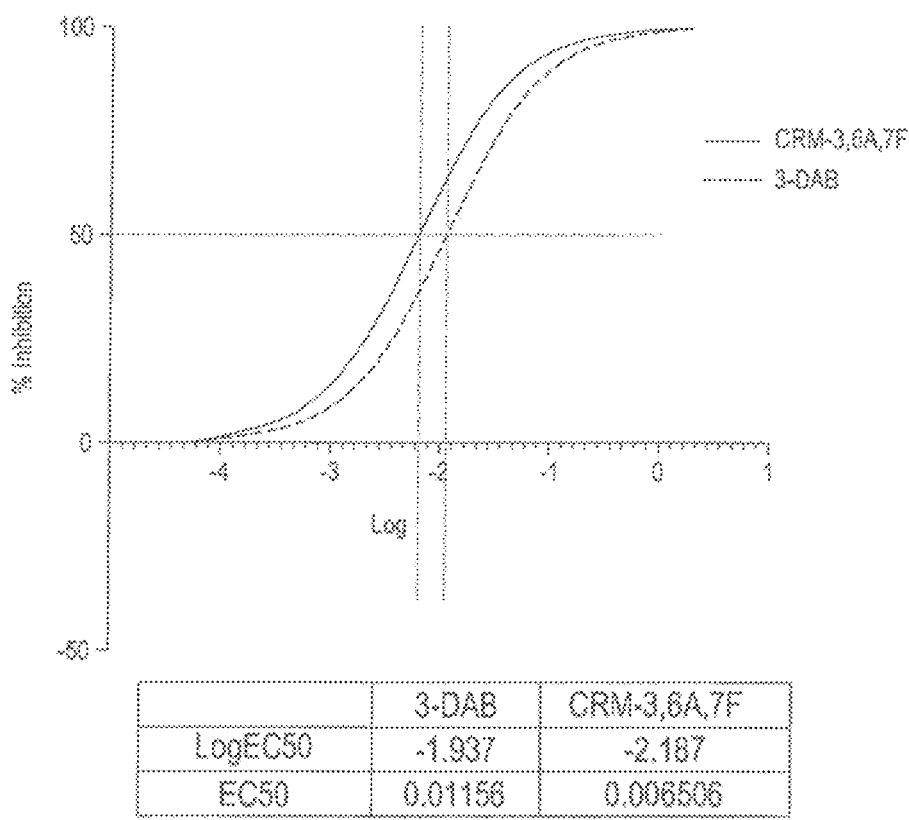

FIG. 18 shows the comparison between the % inhibition (expressed as MIC$_{50}$) of Ps 3-DAB and CRM-3,6A,7F vs. native Ps3 showing Type 1 Antigenicity or Antigenic Identity of Ps3 following either DAB activation or conjugation. FIG. 19 shows the sigmoidal curve (log scale) referred to the graph of FIG. 18.

Figure 20:
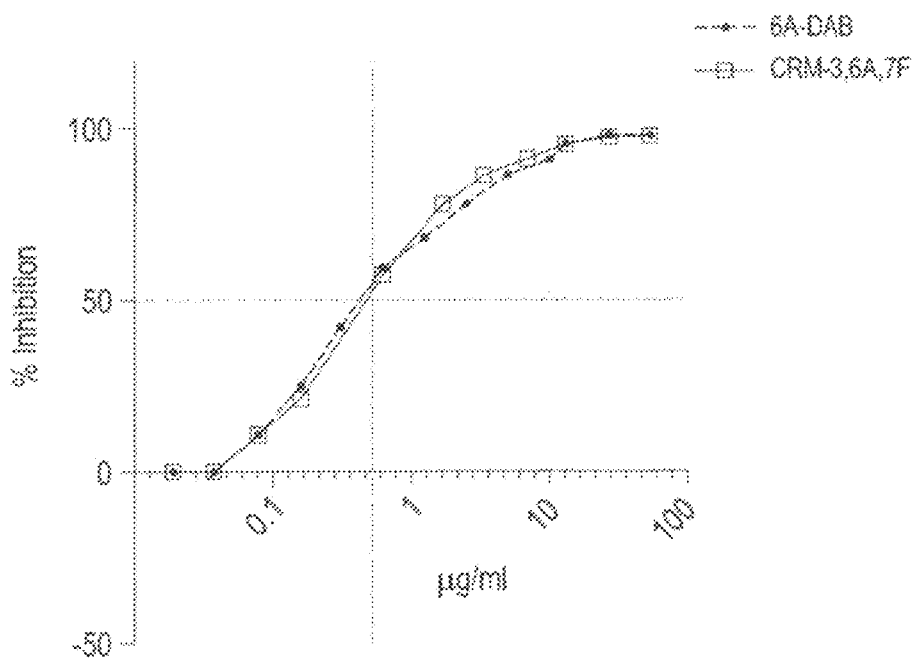
Figure 21:
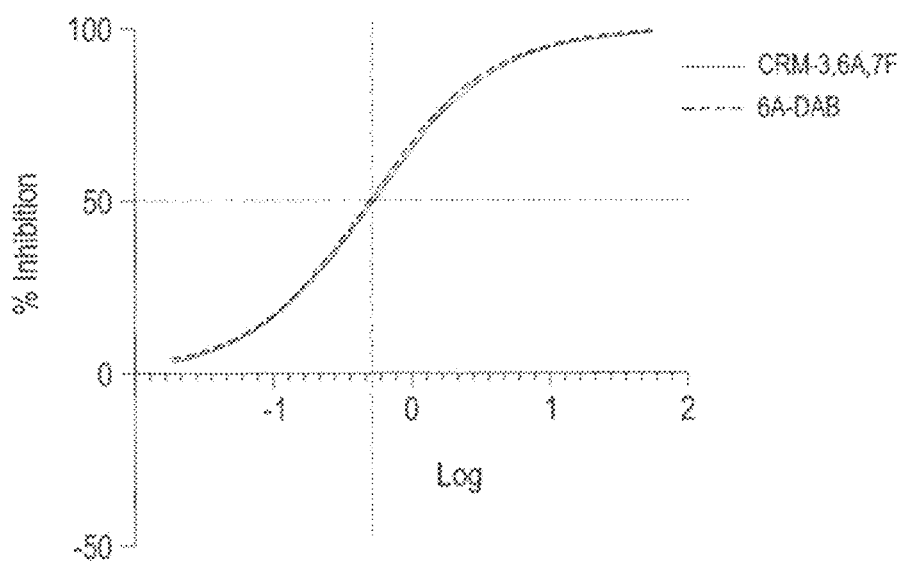

FIG. 20 shows the comparison between the % inhibition (expressed as MIC$_{50}$) of Ps 6A-DAB and CRM-3,6A,7F vs. native Ps 6A showing Type 1 Antigenicity or Antigenic Identity of Ps6A following either DAB activation or conjugation FIG. 21 shows the sigmoidal curve (log scale) referred to the graph of FIG. 20.

Figure 22:
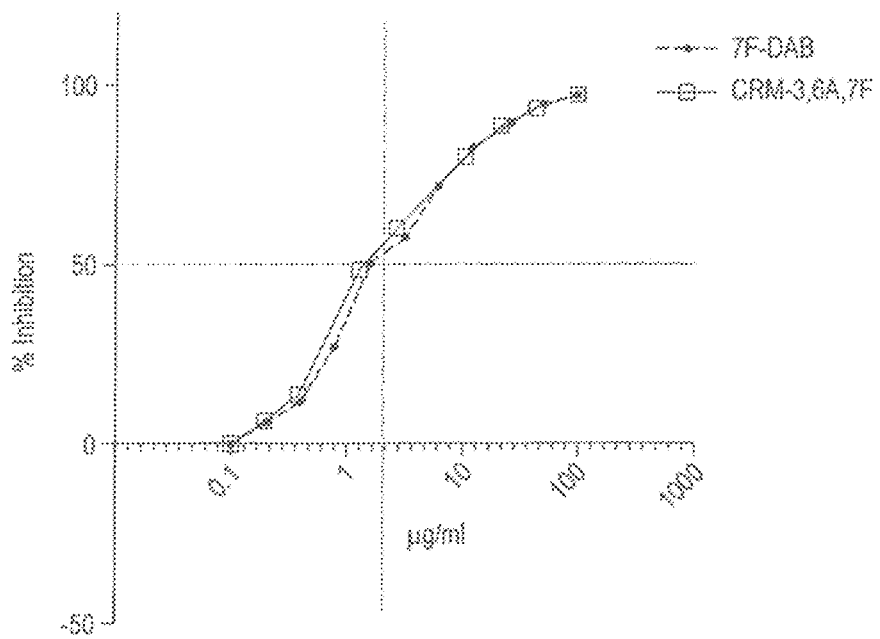

FIG. 22 shows the comparison between the % inhibition (expressed as MIC$_{50}$) MIC50 of Ps 7F-DAB and CRM-3, 6A,7F vs. native Ps 7F showing Type 1 Antigenicity or Antigenic Identity of Ps7F following either DAB activation or conjugation.

Figure 23:
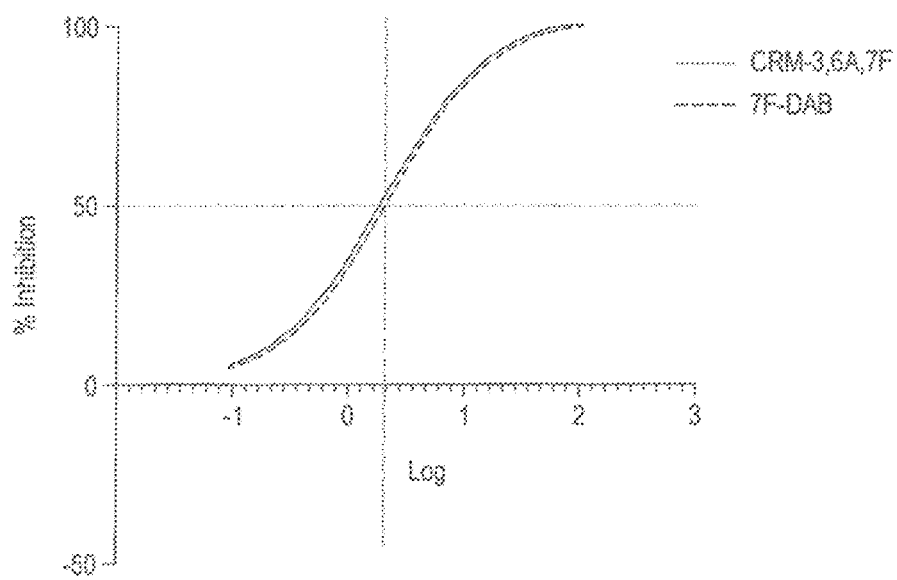

FIG. 23 shows the sigmoidal curve (log scale) referred to the graph of FIG. 22.

In the following experimental section the invention will be disclosed in more detail according to preferred embodiments, that should be considered not to be limitative for the scope of protection but merely for illustrative purpose.

EXAMPLES

Example 1: Synthesis of the Tetravalent Conjugate Antigen Comprising Polysaccharides 3, 6A, IF of S. pneumoniae and the Carrier Protein CRM197

Chemical activation of Ps 3,6A,7F to the homologous Ps-DAB (diamine butyric acid derivative)

This step has been performed according to the process disclosed by the Applicant in the claim 1 (step A1) of the above mentioned patent EP1501542, herewith included as a reference.

Specific controls of such activation as well as the obtained characteristics of the activate Ps structures is here below reported using $^1$H-NMR spectroscopy.

$^1$H-NMR analysis of Ps3-DAB, Ps6A-DAB, Ps7F-DAB

1. Solution of Ps and Ps-DAB Derivatives for NMR Analysis 3-4 mg of polysaccharide sample (PS) or PS-DAB is solved in 0.7 ml of D$_2$O—phosphate buffer and transferred into a 5 mm NMR tube. The concentration of phosphate buffer prepared in D$_2$O is 100 mM, pH=7. Trimethylsilyl-propionic acid sodium salt (TSPA), (CH$_3$)$_3$Si(CD$_2$)$_2$COONa is used as an internal reference. The concentration of TSPA is 1 mM.

2. NMR Equipment

High field NMR spectrometer (600 MHz) is used. A high resolution 5 mm probehead with z-gradient coil capable of producing gradients in the z-direction (parallel to the magnetic field) with a strength of at least 55 G·cm$^{-1}$ is employed.

3. Setup of NMR Experiments

After the introduction of the sample inside the magnet all the routine procedures have been carried out: tuning and matching, shimming, 90 degree pulse calibration. Presaturation can be used to suppress the residual HDO signal. For good presaturation the centre of the spectrum (O1) must be set exactly on the HDO signal (about 4.80 ppm), and good shimming is desirable as well.

After adjustment of parameters for presaturation, the parameters of diffusion gradient experiments are checked. The stimulated echo pulse sequence using bipolar gradients with a longitudinal eddy current delay is used.

4. Fingerprinting of DAB-Activation

Group —CH$_2$—NH$_2$ at 3.08 ppm

Group —CH$_2$—NH—CH$_2$— at 3.17 ppm

5. % of DAB Activation on Ps

Is in the range value of 0.5-5.0% moles DAB/moles BRU (Basic Repeating Unit of the Group-specific Ps) with an optimal molar range 1.5-3.0%.

Derivatization of Ps3-DAB, Ps6A-DAB, Ps7F-DAB to their homologous active esters as Ps-DAB-MSE derivatives This step has been performed according to the process disclosed by the applicant in claim 8 of the European Patent EP 1501542, herewith included as a reference.

Simultaneous coupling of the three activated (poly-functional) Ps to the (poly-functional) carrier protein CRM197

The chemical synthesis of the conjugate, also known as coupling reaction, has been performed according to the process disclosed by the applicant in claim 8 of the European Patent EP1501542 herewith included as a reference.

The procedure, however, can be here considered as innovative because the three coupling reactions are simultaneously run, rather than proceeding in one coupling reaction at the time (or step-by-step process).

This procedure may be preferred to the step-by-step coupling of each Ps-activated antigen for the simple reason of shorting the reaction time, therefore improving the efficiency of the reaction, provided that the three activated-Ps are in the condition to comparatively compete at the equilibrium for the coupling reaction (this feature include comparable average MW, comparable range of Ps-DAB activation and comparable stoichiometric ratios among the reacting groups of the protein and those of the activated Ps). The appropriate stoichiometry of reaction keeps in consideration the total amount of succinimidyl esters relative to the three Ps antigens activated and the amino groups of the carrier protein available.

Stoichiometry is preferentially set as to consider the reactivity of no more than 20% (or 8 out of 40) of the amino groups available in the structure of CRM197 (as an example) in order for the protein to optimally conserve its antigenic repertoire.

Based on experimental data, the coupling reaction is consistent with the following stoichiometry:

CRM197+4 Ps-DAB-derivatives CRM197-(Ps)$_3$+Ps-DAB-derivatives

Where the entity Ps-DAB-derivatives refer to the total of equal parts of each of the three type-specific carbohydrate structures in reaction yielding a conjugate averaging 1 mole of protein for the total of 3 moles of type-specific Ps carried, plus the due excess of Ps-DAB-derivatives, as ruled by the equilibrium constant:

$$K_{eq} = \frac{[CRM197\text{-}(DAB\text{-}Ps)_3][Ps\text{-}DAB\text{-derivatives}]}{[CRM197][Ps\text{-}DAB\text{-derivatives}]^4} = \frac{[CRM197\text{-}(DAB\text{-}Ps)_3]}{[CRM197][Ps\text{-}DAB\text{-derivatives}]^3}$$

The chemical equation makes evidence for the complete glycosylation of the CRM197 carrier protein. The equation also shows that the conjugation reaction depends from the concentrations of both reagents, the nucleophile (CRM197 through the epsilon-$NH_2$ groups of its Lys residues) and the electrophile (the carbonyl moiety of the ester groups of Ps-DAB-derivative) therefore being defined as $S_N2$ reaction.

The above considerations are consistent with the experimental observation that the highest yield in the glycosylation reaction obtained with CRM197 as carrier protein has been 100% of the carrier protein and about 80% (w/w) of the Ps-DAB-derivatives present in reaction, with the remaining part of them being a low amount of uncoupled Ps-derivatives necessary for pushing to the right side the equilibrium.

In this type of reactions, the solvent affects the rate of reaction because solvents may or may not surround the nucleophile, thus hindering or not hindering its approach to the carbon atom. Polar aprotic solvents, are generally better solvents for this reaction than polar protic solvents because polar protic solvents will be solvated by the solvent's hydrogen bonding for the nucleophile and thus hindering it from attacking the carbon with the leaving group. A polar aprotic solvent with low dielectric constant or a hindered dipole end, will favor $S_N2$ manner of nucleophylic substitution reaction (preferred examples are: DMSO, DMF, tetrahydrofuran etc.). However, in the present case using CRM197 as carrier protein, polar protic solvents and polar aprotic solvents work very well when experimentally compared vis-à-vis.

The temperature of the reaction, which affects $K_{eq}$, is the lowest compatible with the use of the solvent chosen, when considering that the reaction is a spontaneous one (therefore being exothermic) and therefore is generally set between a temperature of 4° and 20° C.

In addition to the conjugation chemistry above detailed, other chemistries can be used to achieve the synthesis of the multivalent conjugate antigen; among these, the direct coupling of the protein (via reductive amination) to the oxidized Ps (via O-de-hydrogen uncoupling) or the use of heterologous and chemically complementary linkers that may serve to activate the Ps and the protein.

Also, in addition to the strategy of using chemistries leading to obtain multivalent cross-linked protein-Ps conjugates via the poly-functionality of the protein and that of the Ps components, one may consider the synthesis of the presently disclosed antigenic multivalent molecular construct as based on oligosaccharides activated at their end-reducing group for then being coupled to the carrier protein, as the applicant did show earlier in another model of conjugate antigen in the above mentioned paper Porro M. et al. in Molecular Immunology, 23: 385-391, 1986, herewith enclosed as a reference.

Finally, the disclosed molecular construct might be thought to be prepared by enzymatic glycosylation in bacterial or yeast cells or other engineered living cells, using "ad hoc" DNA-recombinant techniques.

Example 2: Physical-Chemical Analysis of the Antigenic Multivalent Molecular Construct CRM197-3, 6A, 7F The GPC (Gel Permeation Chromatography) analysis has been employed to perform the physical analysis of the antigenic multivalent molecular construct of Example 1. FIG. 10 shows GPC analysis of the multivalent antigen as it is obtained from the conjugation reaction, before purification. The chromatogram comes from Sepharose 4B-CL equilibrated in 0.14 M NaCl buffered at pH=7.50. Purification of the multivalent antigen is simply obtained by collecting and pooling the eluted fractions from Kd=0.00 to Kd=0.30.

The technique of SEC-MALLS helps to define the dispersity (Đ) of the molecular system obtained, calculated using the equation $D=M_m/M_n$, where $M_m$ is the mass-average molar mass and $M_n$ is the number-average molar mass and also allows to determine some intrinsic properties of the above molecular system since the intensity of the light scattering angles carries information about the molar mass, while the angular dependence carries information about the size of the macromolecule. In fact, if a given macromolecule of mass M is made up of elements $m_i$, then the basic light scattering equation shows that:

$$<r_g^2> = \sum_i r_i^2 m_i \bigg/ \sum_i m_i = \frac{1}{M} \sum_i r_i^2 m_i$$

where $r_i$ is the distance of element $m_i$ from the center of mass of the molecule of total mass M. According to this equation, the relationship between mass, size, and the quantities measured is defined.

The following Table 1 shows the characterization of the dispersed molecular mass of the above purified multivalent antigen (fractions in the range Kd=0.00-0.30) analyzed by SEC-MALLS.

TABLE 1

| Upper Mass (g/mol) | Average Mass (g/mol) | Lower Mass (g/mol) |
|---|---|---|
| 5.92 × 10$^6$ (66.4%) | 9.67 × 10$^5$ (26.6%) | 2.69 × 10$^5$ (7.0%) |

The experimental data collected by SEC-MALLS show that the dispersed mass of the antigenic multivalent molecular construct encompasses the basic unit [CRM197-3,6A,7F]$_{n=1}$ for about 7% of the mass dispersion, and polymers of it with composition [CRM197-3,6A,7F]$_{n}$=3.6, for about 27% of the mass dispersion, and up-to [CRM197-3,6A,7F]$_{n=22}$ for the rest of the mass dispersion which represents the main form (66%) of the molecular construct in terms of product of reaction. Polymers of the basic unit of the molecular construct are obtained as cross-linked molecular entities because of the polyfunctionality of the Ps antigens (about 2% of DAB activation, on molar basis, as shown by $^1$H-NMR spectroscopy) and the polyfunctionality of the carrier protein (40 reactive amino groups/mole, available as 39 Lysine residues+1 amino terminal aa within the structure encompassing the whole 535 aa of the sequence).

FIG. 11 shows the GPC analysis, as an example, on the same gel Sepharose 4B-CL of the four components just mixed together (CRM197+Ps 3-DAB+Ps 6A-DAB+Ps 7F-DAB) in order to show absence of any significant amount of complex formation among the single antigens. Chemical methods for titration of the three Ps structures involved the analysis of uronic acid (type 3), phosphorous (type 6A) and hexosamines (type 7F) according to the requirements of the WHO guidelines. The following Table 2 shows the characterization of the dispersed molecular masses of the three mixed type-specific Ps-DAB derivatives as analyzed by SEC-MALLS, for reference.

TABLE 3

| Upper Mass (g/mol) | Average Mass (g/mol) | Lower Mass (g/mol) |
|---|---|---|
| 2.75 × 10$^5$ (17.0%) | 7.27 × 10$^4$ (70.5%) | 1.81 × 10$^4$ (12.5%) |

Considering the different BRU of the three PS structures, the mean number ± SD of BRU/Ps is 112 ± 62

FIG. 12 shows SEC-HPLC analysis of the multivalent antigen, following purification on Sepharose 4B-CL, with specific reference to the profile of the carrier protein CRM197.

The following experimental conditions were used in the SEC-HPLC analysis:
Column: Phenomenex, Biosep-SEC-S3000, 300×7.80 mm (Vo 6.92 min.; Vt 12.5 min.)
MW Sizing range: 700 K-5 K
Eluent: NaCl 0.14M+NaH$_2$PO$_4$ 0.05M pH 6.80
Flow: 1 ml/min
Detector: 280 nm (detection of the protein CRM197 FIG. 13 shows SEC-HPLC analysis of CRM197 as native protein, when mixed with Ps 3-DAB, Ps 6A-DAB and Ps 7F-DAB. Experimental conditions are the same as above reported for the analysis carried out in FIG. 12.

In light of the above the conjugate under analysis is a polydispersed, monomeric to polymeric, molecular entity which contains the basic unit of the molecular construct reported in the chemical equation [CRM197-(Ps) 3], with a calculated average MW of ca. 2.7×10$^5$ when considering the average MW (estimated by SEC-MALLS) of the polyfunctional DAB-activated Ps structures (ca. 0.7×10$^5$) and that of CRM197 (5.85×10$^4$) accounting for 535 aa); accordingly, the several cross-linked units of such basic structure is reaching a MW of ca. 6 millions as evaluated by SEC-MALLS. The w/w ratio between the carrier protein and each of the three type-specific Ps is ca. 1.0; this w/w ratio yields an average molar ratio (R) protein/type-specific Ps of 1.0, corresponding to an average ratio of one mole of protein/mole of type-specific Ps, as well suggested by the chemical equation.

Accordingly, the experimentally obtained, cross-linked, molecular entity responds to a molecular model constituted by several polymeric units of the basic unit just consisting of one mole of carrier protein carrying a total of three moles of type-specific Ps (one mole for each type-specific Ps).

Example 3: Immunochemical Analysis of the Antigenic Multivalent Molecular Construct CRM197-3,6A,7F The immunochemical analysis of the antigenic multivalent molecular construct CRM197-3,6A,7F was carried out by SDS-PAGE using the analytical conditions according to Laemmli U.K., Nature 227, 680-685 (1970), herewith enclosed as reference.

FIG. 14 shows the SDS-PAGE analysis (9% Glycine buffer) showing the pattern of the purified multivalent antigen.

FIG. 15 shows immunoblot analysis (Western-blot) of the multivalent antigen as qualitatively revealed by type-specific serum polyclonal antibody. The analytical conditions employed were according to Towbin H. et al., PNAS 76: 4350-4354 (1979). Silver staining according to Porro M. et al., Anal. Biochem. 118: 301-306 (1981). The serum polyclonal, Ps type-specific, antibodies are described in the below section dedicated to the inhibition-ELISA method.

Qualitative and quantitative determination of each antigenic Ps component on the basis of inhibition-ELISA using polyclonal (or monoclonal) antibodies As well known since the birth of Immunochemistry, branch of the wider field of Immunology in the Thirties' of the past Century, capsular Ps antigens are composed of Basic Repeating Units (BRU) which may be constituted by homologous monosaccharides (e.g.: meningococcal Ps) as well as by more complex hetero-polysaccharide sequences involving bi/tri/tetra/penta/esa/epta-saccharide residues (e.g.: pneumococcal Ps). An average sequence of 5 (preferably 8) to 12 monosaccharide residues form the basic structural epitope of (Ps) carbohydrate antigens, which confer the due immunological specificity to each (Ps) structure. This size, typical of a single epitope within the human ABO system or of a sequence of epitope-repeating structures within complex bacterial capsular Ps, is coherent with the size of the binding site of an antibody (Kabat E. A., "The nature of an antigenic determinant" J. Immunol. 97: 1-11, 1966) and, on these basis, it was possible to describe the reactivity of a Ps structure toward a specific polyclonal population of antibodies, by inhibiting the binding reaction of the system Ps-Ab using different MW of the Ps polydispersed system, in order to document the relation existing between antigenicity of a Ps structure containing repeating BRU (thus forming repeated epitopes of identical antigenicity) and the specificity for it of the homologous polyclonal antiserum (Porro M. et al, Mol. Immunol. 22: 907-919, 1985); by comparison of the MIC50 of the various MW of the polydispersion of a given Ps, it was then possible to define the relative specificity of a polyclonal (or monoclonal) population of antibodies for such MW and finally calculating the relative concentration of the different Ps structures for a quantitative determination of it.

By having a reliable immunochemical method for mapping and titering the Ps structures present in such a molecular construct, there are practical advantages of determining the qualitative and quantitative characteristics of such model of conjugates, over the chemical methods, especially in cases of Ps with very close structural features for their sequences, like in the case of type 6A and 6B or type 19A and 19F or in any other case where structural similarities among Ps antigens are present as in the case of type-specific Ps belonging to a given reference group (e.g.: Group 6 includes the type-specific Ps 6A,6B,6C,6D; Group 19 includes the type-specific Ps 19A,19B,19C,19F; Group 23 includes the type-specific Ps 23A,23B,23F). In fact, the exquisite specificity of an antibody can easily discriminate between such structural similarities without ambiguity and in short time, unlike chemical methods.

The recent development of monoclonal antibodies to the Ps antigens of S. pneumoniae (Pride M. W. et al., Clin. And Vaccine Immunol. 19(8): 1131-1141, 2012) would further increase the potential of this powerful method of analysis.

The comparison between chemical titration and immunochemical titration of carbohydrate antigens for testing their quantitative equivalence, is performed by the use of inhibition-ELISA, through the experimentally determined parameter $MIC_{50}$ (Minimal Inhibitory Concentration of the selected carbohydrate antigen working as inhibitor of the homologous reference Ps-Ab reaction) in order to evaluate accuracy and precision of the immunochemical method with respect to the chemical one in the analytical control of such a kind of molecular construct.

Inhibition-ELISA Protocol

The following ELISA protocol was applied in order to determining the value of $MIC_{50}$ of each of the three Ps-DAB derivatives and the protein CRM197 or the multivalent conjugate CRM197-3,6A,7F as inhibitors of the homologous reference reaction type-specific Polysaccharide-Antibody (Ps-Ab) or Protein-Antibody (Prot-Ab).

Reference type-specific Ps-derivative (Ps-DAB) and the multivalent conjugate CRM197-3,6A,7F were prepared according to the mentioned process reported by Porro M. in claim 8 of the Patent EP1501542.

Chemical methods for titration of the three Ps structures involves analysis of Uronic acid (type 3), Phosphorous (type 6A) and Hexosamines (type 7F) according to the requirements of the WHO guidelines. The inhibition reaction is based on the principle for a given carbohydrate structure, of a given molecular mass, of inhibiting the homologous reference reaction system according to the immunochemical equation:

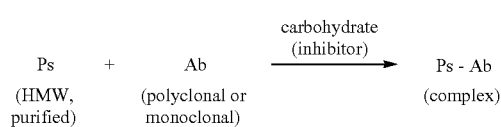

So that the difference in reactivity between the reference reaction and the inhibited-one is representative for the different or identical specificity of the antibody population for the inhibitor. By using carbohydrate structures of different molecular mass, one can describe the sigmoidal curve typical of that specific reaction and calculate the $MIC_{50}$ of the inhibitor for then comparing it with the one of the carbohydrate structure of reference and establishing the parameter of Antigenicity of the inhibitor (on qualitative basis) and Specificity of the antibody (on quantitative basis). All these concepts and the relative practical use are reported in the following publications, herewith incorporated as references:

Berzofsky J. A. and Schechter A. N. Mol. Immunol., 18: 751-763 (1981);

Porro M. et al. Mol. Immunol., 22: 907-919 (1985).

Method of Analysis (Illustrative)

Stock Solutions:

Ps-DAB or CRM197 at 1 mg/ml in PBS pH 7.2-7.4
  PBS 1× (1 L)
    8.0 g NaCl
    0.31 g $KH_2PO_4$
    2.06 g $Na_2HPO_4.7H_2O$
    0.16 g KCl
    Do not adjust pH
  TBS-Brij 0,1% (v/v)
    TBS 10× (1l)
      80 g NaCl
      1.6 g KCl
      0.94 g Tris
      14.56 g Tris-HCl
      33 ml Brij-35 (30% v/v)
      Stable at r.t. for 12 months
      Dilute 50 ml buffer to 500 ml
      MilliQuf water
  PBS-Tween20 0.05% (v/v)
  Goat Anti-Mouse IgG or IgM peroxidase labeled
  Phosphate-Citrate Buffer 0.05M pH 5.0
  $H_2O_2$ 30% (v/v)
  0-Phenilenediamine 1 mg/ml in Phosphate-Citrate Buffer 0, 05M pH 5.0
  $H_2SO_4$ 3M Procedure:

1. Coating Plates (GREINER 65001 polystyrene plate SIGMA cod. M4436)
  Ps at 20 µg/ml PBS pH 7.4 37° C. 2 h+o.n. 4° C.
  CRM197 at 10 µg/ml PBS pH 7.4 o.n. 4° C.
  Coat 100 µl/well 2. Washing 5× with TBS-Brij 0,1% (v/v) ($1^{st}$ wash 20 sec.)

3. Pneumococcal reference polyclonal antisera from Statens Serum Institute, Copenhagen, DK (www.ssi.dk) in PBS-Tween 0.05% (v/v) 2h 37° C. Final dilutions (as examples):
  a. Rabbit antiserum to group 3 1:100,000 v/v (Positive~1.0 $OD490_{nm}$)
  b. Rabbit antiserum to group 6A1:25,000 v/v (Positive~1.0 $OD490_{nm}$)
  c. Rabbit antiserum to group 7F 1:800,000 v/v (Positive~1.0 $OD490_{nm}$)

4. Unknown samples: the unknown samples are interpolated versus the reference sigmoidal regression curve obtained by the reference reaction.

5. Murineserum anti-CRM197, final dilution, 1:100,000 v/v (Positive −1.0 $OD490_{nm}$).

TABLE 3

| Inhibitor final/well | 1 ng/ml | 10 ng/ml | 100 ng/ml | 1 μg/ml | 10 μg/ml | 100 μg/ml | 200 μg/ml | 400 μg/ml | 1 mg/ml | 2 mg/ml | Anti-Ps stock solution |
|---|---|---|---|---|---|---|---|---|---|---|---|
| 0.5 ng/ml | 50 μl | | | | | | | | | | 50 μl |
| 5 ng/ml | | 50 μl | | | | | | | | | 50 μl |
| 50 ng/ml | | | 50 μl | | | | | | | | 50 μl |
| 0.5 μg/ml | | | | 50 μl | | | | | | | 50 μl |
| 5 μg/ml | | | | | 50 μl | | | | | | 50 μl |
| 50 μg/ml | | | | | | 50 μl | | | | | 50 μl |
| 100 μg/ml | | | | | | | 50 μl | | | | 50 μl |
| 200 μg/ml | | | | | | | | 50 μl | | | 50 μl |
| 500 μg/ml | | | | | | | | | 50 μl | | 50 μl |
| 1 mg/ml | | | | | | | | | | 50 μl | 50 μl |

6. Incubation x Inhibition time: 15 min
7. Washing 5× with TBS-Brij 0.1% (v/v) (1$^{st}$ wash 20 sec.)
8. Goat Anti-Rabbit or anti Mouse IgG peroxidase labelled in PBS-Tween 0.05% (v/v) 2h 37° C.
9. Washing 5× with TBS-Brij 0.1% (v/v) (1$^{st}$ wash 20 sec.)
10. O-Phenilenediamine 1 mg/ml in Phosphate-Citrate Buffer 0.05M pH 5.0, $H_2O_2$ 0.03% (v/v)
11. After 5' Stop the reaction with $H_2SO_4$ 3M 50 μl/well
12. Read at OD 490 nm
13. Interpolate unknown values vs the reference sigmoidal line regression obtained by the reference reaction:

Calculation of % Inhibition:

$$\frac{\text{Inhibited } OD \text{ Value-Blank } OD \text{ value}}{\text{Positive } OD \text{ Value-Blank } OD \text{ value}} \times 100 = (\%)$$

Thus, % Inhibited=100−(%)

Calculation of $MIC_{50}$:

This inhibitory concentration is determined at 50% of either the regression function or the related sigmoidal curve. Method's SD is within 20% of the mean value. RESULTS The results of the MIC50 for CRM197 native and in its conjugated form as CRM197-Ps,3,6A,7F show that the conjugation reaction did not affect the antigenic features of CRM197 (Type 1 Antigenic Identity), as may be inferred from the analysis of the graphs set forth in FIG. 16-17. FIG. 17 illustrates the non-linear regression function of the sigmoidal curve.

The results of the MIC50 for each of the three conjugated Ps-DAB derivatives are illustrated in the graphs set forth in FIGS. 18-23. FIGS. 19, 21 and 23 illustrate the non-linear regression function of the sigmoidal curve.

Example 4: Determination of the Concentration for the Carbohydrate Antigen in Either Activated or Multivalent Conjugated Form: Comparison of Chemical Titration Vs. Immunochemical Titration Immunochemical titers are obtained according to the method reported above in Example 3 dedicated to the Inhibition-ELISA method; chemical titers are obtained according to the methods above reported in Example 2; immunochemical titers of unknown samples of each of the three carbohydrate-specific antigens, either in activated or conjugated form, were determined by interpolation on the linear part of a reference standard curve built by inhibition-ELISA using known, chemically titred, carbohydrate antigen amount. The reported values are the mean of several independent assays. Results on determination of quantitative equivalence of the two methods are summarized in the following Table 4.

TABLE 4

| | Chemical determination (μg/ml) | Immunochemical determination* (μg/ml) |
|---|---|---|
| Ps1 | 1.0 | 0.9 (−10.0%) |
| | 2.0 | 2.3 (+13.1%) |
| | 4.0 | 3.7 (−7.5%) |
| *Lowest amount Ps1 detected: 0.02 ug | | |
| Ps3 | 0.80 | 0.91 (+13.4%) |
| | 1.60 | 1.77 (+10.6%) |
| | 3.20 | 3.31 (+3.4%) |
| | 6.40 | 6.71 (+4.8%) |
| *Lowest amount Ps3 detected: 0.01 ug | | |
| Ps4 | 2.0 | 2.25 (+11.2%) |
| | 4.0 | 3.80 (−5.0%) |
| | 8.0 | 7.40 (−7.5%) |
| *Lowest amount Ps4 detected: 0.01 ug | | |
| Ps5 | 3.1 | 3.3 (+6.1%) |
| | 6.25 | 5.7 (−8.8%) |
| | 12.5 | 10.8 (−13.6%) |
| *Lowest amount Ps5 detected: 0.015 ug | | |
| Ps6A | 0.63 | 0.60 (−4.8%) |
| | 1.72 | 1.92 (+11.6%) |
| | 3.43 | 3.63 (+5.8%) |
| | 6.87 | 7.31 (+6.4%) |
| *Lowest amount Ps6A detected: 0.01 ug | | |
| Ps6B | 2.0 | 2.4 (+16.7%) |
| | 4.0 | 4.3 (+7.0%) |
| | 8.0 | 9.2 (+13.0%) |
| *Lowest amount Ps6B detected: 0.10 ug | | |
| Ps7F | 1.34 | 1.43 (+6.7%) |
| | 2.68 | 3.00 (+11.9%) |
| | 5.37 | 5.47 (+1.9%) |
| | 10.75 | 11.07 (+3.0%) |
| *Lowest amount Ps7F detected: 0.01 ug | | |
| Ps9V | 3.8 | 4.2 (+9.6%) |
| | 7.5 | 6.4 (−15.0%) |
| | 15.0 | 12.2 (−18.7%) |
| *Lowest amount Ps9V detected: 0.10 ug | | |
| Ps14 | 3.4 | 3.8 (+10.6%) |
| | 6.8 | 6.5 (−5.0%) |
| | 13.5 | 16.2 (+16.5%) |
| *Lowest amount Ps14 detected: 0.10 ug | | |
| Ps18C | 2.5 | 2.8 (+10.8%) |
| | 5.0 | 4.7 (−6.0%) |
| | 10.0 | 8.9 (−11.0%) |
| *Lowest amount Ps18C detected: 0.02 ug | | |
| Ps19A | 3.8 | 4.1 (+8.7%) |
| | 7.5 | 6.5 (−13.4%) |
| | 15.0 | 13.3 (−11.4%) |
| *Lowest amount Ps19A detected: 0.02 ug | | |
| Ps19F | 3.8 | 3.5 (−7.9%) |
| | 7.5 | 8.3 (+9.4%) |
| | 15.0 | 17.0 (+11.8%) |

TABLE 4-continued

| | Chemical determination (μg/ml) | Immunochemical determination* (μg/ml) |
|---|---|---|
| *Lowest amount Ps19F detected: 0.02 ug | | |
| Ps23F | 3.8 | 4.3 (+11.7%) |
| | 7.5 | 6.6 (−12.0%) |
| | 15.0 | 13.3 (−11.4%) |
| *Lowest amount Ps23F detected: 0.02 ug | | |
| $CRM_{197}$ | 1.3 | 1.2 (−7.7%) |
| | 2.5 | 2.7 (+11.7%) |
| | 5.0 | 5.3 (+5.7%) |
| | 10.0 | 9.6 (−4.0%) |
| *Lowest amount $CRM_{197}$ detected: 0.10 ug | | |

*Lowest amount immunochemically detectable for the type-specific Ps in the assay conditions.
Note:
Physical-chemical determination of the protein CRM197 was performed by Folin reagent and/or amino acid analysis using hydrophobic reverse-phase HPLC to separate fluorescein-labeled amino acids following acid hydrolysis (Pico-Tag method by Millipore). SD for the physical-chemical determinations is within 10% of the mean values; SD for the immunochemical determinations is within 20% of the mean values, that is within the estimated SD of the day-by-day variation of the ELISA method and in agreement with the guidelines of the European Pharmacopoeia 5th Edition (2008) for the Pneumococcal Polysaccharide Conjugate Vaccine.

The same methodology described for the qualitative and quantitative immunochemical analysis of each molecular construct above reported, is then used for characterization of the final formulation of the polyvalent vaccine containing the association of several (4 or 5 or 6 or more) molecular constructs in order to get the complete characterization of an exemplificative 12-valent or 15-valent or 18-valent vaccine.

Example 5: Immunological Analysis in a Murine Model of the Antigenic Multivalent Molecular Construct, as an Example Vaccine Formulation Mean ratio Protein/each of the type-specific Ps: 1.1±0.1 (w/w).

Dose of the molecular construct CRM197-3,6A,7F

The injected dose is 0.01 μg and 0.1 μg of each type-specific conjugated Ps, with and without $AlPO_4$ as adjuvant at the fixed dose of 0.5 mg/dose (equivalent to ca. 0.120 mg of Alum). Adsorption of the multivalent molecular construct to the mineral adjuvant occurred at ≥80%, on weight basis, as estimated by ELISA. According to the stoichiometry of the multivalent conjugate, the total dose of CRM197 is ca. 0.01 μg in the case of the lowest dose of each type-specific conjugated Ps and ca. 0.1 μg in the case of the highest dose of each type-specific conjugated Ps.

It is remarked that the dose injected of 0.01 μg Type-specific Ps is the lowest-one, immunogenic in mice, which is acknowledged by US-FDA and EMEA for the currently licensed pneumococcal conjugate vaccines, which use Aluminum Phosphate as adjuvant.

Animals

Each group of animals containing 10 female Balb/c mice (alternatively CD1) and 6 female New Zealand white rabbits.

Route i.p. (mice) and s.c. (rabbits)

Immunization schedule 0, 2, 4 weeks; bleeding at week 0, 2, 4, 6 (mice).

0, 4 weeks; bleeding at week 0, 4, 6 (rabbits).

Control immunization with plain Ps antigens were omitted on the basis of the historical knowledge that highly purified Ps antigens are not significantly immunogenic in mammalians and do not "boost" IgG isotype antibodies following repeated injections of it.

ELISA Titers

Titers expressed as end-point reaction showing O.D.≥2.0 relative to the control reactions for each type-specific Ps and CRM197 or DT (Diphtheria Toxoid), the antigen immunogenically identical and in statistical correlation with CRM197 (Porro M. et al. J. Infect. Dis., 142 (5), 716-724, 1980). Sera pool dilutions are performed serially, in twofold fashion, starting from dilution 1/200.

MOPA (Functionality Assay)

For testing Opsonic activity of the murine and rabbit polyclonal antibodies raised following immunization with the multivalent molecular construct, the MOPA-4 test (4-fold Multiplexed Opsono Phagocytic killing assay) was run, as recommended by WHO guidelines, using HL60 cells. Titers expressed as geometric mean of the end-point dilution showing ≥50% killing activity for each sera pool at each dose, as referred to a standard curve built in parallel for calculating the titer values of the various samples by linear interpolation.

Immunological Results

Dose of 0.01 μg Ps/type-specific conjugated Ps. Geometric Mean Titers of IgG or IgM to type-specific Ps or to CRM197 in murine sera pool as determined by ELISA. SD is within ±25% of the reported Geometric Mean. MOPA titers are reported in parenthesis as calculated by linear interpolation in the assay procedure. Unless otherwise indicated, the statistical significance among sera titers (determined by t-test) was <0.01. Results are summarized in the following Table 5.

TABLE 5

| | Without Adjuvant | | | | With Adjuvant | | | |
|---|---|---|---|---|---|---|---|---|
| Ag | W0 | W2 | W4 | W6 | W0 | W2 | W4 | W6 |
| 3 | <200 | <200 | 200 | 800 | <200 | 200 | 800 | 3,200 |
| | | | | | <200 | <200 | <200 | <200 |
| | | | | | | | (12) | (124) |
| 6A | <200 | <200 | 200 | 800 | <200 | 200 | 400 | 3,200 |
| | | | | | <200 | <200 | <200 | <200 |
| | | | | | | | (6) | (135) |
| 7F | <200 | <200 | 200 | 800 | <200 | 200 | 1,600 | 6,400 |
| | | | | | <200 | <200 | <200 | <200 |
| | | | | | | | (26) | (248) |
| CRM197 | <200 | <200 | 800 | 3,200 | <200 | 1,600 | 12,800 | 25,600 |
| | | | | | <200 | 200 | 800 | 800 |

Dose of 0.10 μg/type-specific conjugated Ps. Geometric Mean Titers of IgG or IgM to type-specific Ps or to DT in murine sera pool as determined by ELISA. SD is within ±25% of the reported Geometric Mean. MOPA titers are reported in parenthesis as calculated by linear interpolation in the assay procedure. Results are summarized in the following Table 6.

TABLE 6

| Type | Without Adjuvant | | | | With Adjuvant | | | |
|---|---|---|---|---|---|---|---|---|
| Ps | W0 | W2 | W4 | W6 | W0 | W2 | W4 | W6 |
| 3 | <200 | 200 | 800 | 6,400 | <200 | 800 | 6,400 | 25,600 |
| | | | | | <200 | 200 | 400 | 800 |
| | | | | | | (16) | (254) | (1,824) |
| 6A | <200 | 200 | 800 | 3,200 | <200 | 800 | 3,200 | 12,500 |
| | | | | | <200 | 200 | 200 | 800 |
| | | | | | | (22) | (120) | (1,150) |
| 7F | <200 | 200 | 1,600 | 3,200 | <200 | 1,600 | 6,400 | 25,600 |
| | | | | | <200 | 200 | 400 | 800 |
| | | | | | | (48) | (168) | (1,580) |

TABLE 6-continued

| Type | Without Adjuvant | | | | With Adjuvant | | | |
|---|---|---|---|---|---|---|---|---|
| Ps | W0 | W2 | W4 | W6 | W0 | W2 | W4 | W6 |
| CRM197 | <200 | 800 | 3,200 | 12,800 | <200 | 6,400 | 25,600 | 102,400 |
|  |  |  |  |  | <200 | 200 | 800 | 1,600 |

The above Tables 5 and 6 show the anamnestic induction of biologically functional IgG isotype antibodies for each of the four components of the multivalent molecular construct.

Particularly, any boosting activity on the immune system observed for the carrier protein is in parallel observed for each of the carried Ps antigens, typical and well known behavior of helper T-dependent antigens. The effect of the mineral adjuvant is particularly evident at such low doses of the multivalent antigen, another feature of helper T-dependent antigens like proteins which do generate a stronger immune response taking further advantage from the antigen slow-release over time in the host's body.

Furthermore, the effect of glycosylation on the carrier protein CRM197, as generally known for glycoproteins, can be beneficial for the improved resistance of this protein to proteolytic enzymes, since CRM197 is a fragile protein when exposed to the serine proteases widely present in mammalians (Porro M. et al., J. Infect. Dis., 142 (5), 716-724, 1980).

The booster effect obtained against CRM197 also strongly supports the fact that the multivalent molecular construct has the potential to work as antigen in humans for the prevention of toxicity due to diphtheria toxin, a well documented property of CRM197 in animal models (see the above bibliographic reference), in which case the multivalent antigen might be also used for the immunization of infants and young children in replacement of the diphtheria toxoid vaccine (present in the DTP vaccine) so that the antigenic burden of the paediatric vaccines in use could be further reduced. Finally, according to the immunological features of helper T-dependent antigens, IgM isotype antibody were neither significantly induced nor boosted by the carrier protein or the carried Ps of the multivalent molecular construct.

Rabbit sera were specifically used to assess the fourfold increase of IgG isotype antibody ELISA titers to type-specific Ps, with the parallel increase of OPA titers, following the first booster dose of the molecular construct. The following results were collected, expressed as fold-increase of the sera GMT obtained with respect to the titers detected following the immunological priming dose and reported in the following Table 7.

TABLE 7

| Type Ps | IgG Ab to Ps (fold increase) | OPA to Ps (fold increase) |
|---|---|---|
| 3 | 12 | 40 |
| 6A | 18 | 48 |
| 7F | 28 | 52 |

Example 6: Vaccine Formulation of a Quadrivalent Meningococcal Conjugate Vaccine (QMCV) and of an Up-to 25-Valent Pneumococcal Polyvalent Conjugate Vaccine (PPCV)

The composition/formulation of QMCV may be limited to one single molecular construct where one mole (or fractions of it) of carrier protein carries at least one mole (or fractions of it) of each of the four different carbohydrate structures. The related pondered amount of the multivalent antigen depends upon the selected MW of the activated carbohydrate structures which may vary from LMW haptens constituted by a few (8-12) monosaccharide residues or BRU (Basic Repeating Units) encompassing the respective basic epitopes [Porro M. et al. Molecular Immunology, 22: 907-919 (1985); Porro M. et al. Molecular Immunology, 23: 385-391 (1986)] and up-to HMW carbohydrate structures composed of 200 BRU or more for containing the repeated structure of the basic epitope.

In such a case the amount of carrier protein per human dose, can be reduced to at least 25% of the amount present in a formulation which uses the association of single, group-specific, conjugates.

The composition of PPCV depends from its polyvalent formulation. For instance, for a 15-valent vaccine containing selected 15 serotypes or for a 18-valent vaccine containing selected 18 serotypes, as above considered, only five to six entities of the multivalent antigenic molecular construct will be necessary, since in each of them, one mole (or fractions of it) of carrier protein will carry an average of one mole (or fractions of it) of each of three different type-specific carbohydrate structures. The related pondered amount of the multivalent antigen depends upon the selected MW of the activated carbohydrate structures which may vary from LMW haptens constituted by a few BRU (Basic Repeating Units) encompassing the respective epitopes (Arndt B. and Porro M. in: Immunobiology of Proteins and Peptides, Edited by M. Z. Atassi, Plenum Press, New York and London, pg. 129-148, 1991) and up-to HMW carbohydrate structures composed of 200 BRU or more for containing the repeating structure of the basic epitope. In any case the amount of carrier protein per human dose, can be reduced to at least 30% of the amount present in a formulation which uses the association of single, type-specific, conjugates.

New emerging serotypes of S. pneumoniae according to the public available data on epidemiology and antibiotic resistance, are type 6C, 6D (Satzke C. et al., J. Clin. Microbiol., 48(11): 4298, 2010; Yao K H et al., Diag. Microbiol. Infect. Dis., 70(3):291-8, 2011); serogroups 11 (type 11A, 11B, 11C, 11F) (Richter S. et al., Clin. Infect. Dis., 48:23-33, 2009); Calix J. J. et al. J. Bacteriol. 193: 5271-5278, 2011); serogroup 15 (type 15B and type 15C); type 23A, serogroups 33 (33F) and 35 (type 35B) (Swanson D., IDSA meeting, Boston, 2011); such antigen Ps might be likely included in a further up-dated broad-spectrum vaccine formulation prepared according to the molecular construct disclosed in the present Application.

While the presently licensed 13-valent vaccine covers about 61% of IPD in children younger than 5 years, an up-dated formulation containing the Ps from the newly emerging types of S. pneumoniae, might well elevate the bar on coverage to 75-80%; in fact, it has been estimated that a formulation containing the 23-valent types of Ps today present in the polysaccharide-based vaccine, accounts for 88% of the bacteremic pneumococcal diseases which then cross-react with types of Ps causing an additional 8% of disease due to S. pneumoniae (source US-Center for Disease Control: www.cdc.gov.). Such kind of up-dated, very broad, formulations can be safely prepared by the use of molecular constructs of the present invention, which allows a reduced use of protein carrier for carrying such an increased number of Ps antigens. For instance, when considering the dose of 2 μg of CRM197 (similar to Prevnar composition)/molecular construct, six molecular constructs carrying 18 Ps antigens would contain a total amount of 12 µg of protein, that is ca. 40% of that present in the 13-valent Prevnar vaccine, composed of single-conjugates of each type-specific Ps antigen. As specifically referred to an exemplified formulation of PPCV containing a 15-valent formulation which includes nowadays the most prevalent, epidemiologically significant, type-specific capsular polysaccharides of *S. pneumoniae*, the following molecular constructs have been synthesized and analyzed as an extended exemplification of the preferred embodiments, according to the methods reported above in Example 1, 2 and 3 for the molecular construct CRM197-3,6A,7F. The total amount of carrier protein exemplified in this exemplified 15-valent vaccine prepared and formulated according to the procedures reported in this application and defined by the stoichiometry of the resulting five molecular constructs, each one expressing built-in multiple epitopes, is coherent with the following molar composition relatively to the dose of each molecular construct containing ca. 1 µg of CRM197 carrier protein (MW=58.5 K) and ca. 1 µg of each of the three selected DAB-activated, type-specific, polysaccharide antigens (average MW=70.0 K based on two different criteria of analysis, that is estimating sizing by molecular filtration on calibrated filter membranes and estimating sizing by SEC-MALLS, in all cases using reference carbohydrate molecules like Dextrans of various MW).

TABLE 8

| Molecular construct | Average (w/w) ratio CRM197/Ps | Average molar ratio CRM197/Ps* |
|---|---|---|
| CRM197-3, 6A, 7F | CRM197/Ps3 = 1.20 | 1.44 |
|  | CRM197/Ps6A = 0.98 | 1.17 |
|  | CRM197/Ps7F = 1.09 | 1.30 |
| CRM197-5, 9V, 19F | CRM197/Ps5 = 1.03 | 1.23 |
|  | CRM197/Ps9V = 0.93 | 1.11 |
|  | CRM197/Ps19F = 1.05 | 1.26 |
| CRM197-1, 14, 19A | CRM197/Ps1 = 1.19 | 1.42 |
|  | CRM197/Ps14 = 0.97 | 1.16 |
|  | CRM197/Ps19A = 0.92 | 1.10 |
| CRM197-22F, 23F, 33F | CRM197/Ps22F = 1.00 | 1.20 |
|  | CRM197/Ps23F = 1.14 | 1.37 |
|  | CRM197/Ps33F = 1.11 | 1.32 |
| CRM197-4, 6B, 18C | CRM197/Ps4 = 1.18 | 1.41 |
|  | CRM197/Ps6B = 1.19 | 1.42 |
|  | CRM197/Ps18C = 1.08 | 1.20 |

In the exemplified molecular constructs, the Mean of the (w/w) Protein/type-specific Ps ratio is: 1.07±0.097 (9.1%) corresponding to the Mean of the (mol/mol) ratio: 1.27±0.12.

In the case when the carrier protein selected is CRM197 and the average MW of each Ps antigen is twice of the above reported value, or 140 K, the molar ratio protein to each Ps increases to an average of 2.5; in contrast, when the average MW of each Ps antigen is half of the above reported value, or 35 K, the molar ratio protein to each Ps decreases to an average of 0.64.

The concept of calculating and comparing the features of conjugate antigens on molar basis is fundamental because the immune system processes antigens on molar basis, as Nature does in each chemical or biochemical reaction of transforming matter, therefore referring to the antigen's MW. Accordingly, depending from the average MW of each type-specific Ps antigen and that of the protein carrier, the molar ratios of conjugate antigens are subject to change by the selection of their antigen components. It is mostly preferred that molar ratios between carrier protein and each type-specific Ps antigen be equal to or higher than 1.0 for a likely optimal expression of helper T-dependency. In addition to this molar parameter, it is also important considering the average amount of covalent bonds interposed between the protein and each type-specific carbohydrate antigen, which parallels the activation rate of the type-specific polysaccharide, since this hybrid molecular region is the one experimentally suggested as responsible for the acquired helper T-dependent properties of a conjugate molecule (Arndt and Porro, 1991).

According to the above considerations, another way to change the stoichiometry, and therefore the molar ratio among the components (the carrier protein and each of the carried carbohydrate antigens) of the molecular construct, without changing the average MW of the Ps antigens selected, is the one which refers to the following exemplified molecular model. This model was synthesized by virtue of a modified stoichiometry in the reagents of the chemical reaction above reported, in favor of the protein component which was present in reaction at the reversed (w/w) ratio of the reaction reported in the above chemical equation, with each of the Ps-activated antigens, in order to make evidence of the flexibility of such chemical reaction which may also lead to a product showing the molar ratio between the carrier protein and the carried Ps antigens in favor of the former component. When referring to the vaccine dose related to the stoichiometry of this exemplified molecular construct, it still contains ca. 1.0 µg of CRM197 carrier protein (MW=58.5 K) but only ca. 0.3 µg of each of the three selected DAB-activated, type-specific, polysaccharide antigens (average MW=70.0 K).

TABLE 9

| Molecular construct | Average (w/w) ratio CRM197/Ps | Average molar ratio CRM197/Ps |
|---|---|---|
| CRM197-3, 6A, 7F | CRM197/Ps 3 = 2.85 | 3.41 |
|  | CRM197/Ps 6A = 3.15 | 3.77 |
|  | CRM197/Ps 7F = 2.70 | 3.22 |
| CRM197-5, 9V, 19F | CRM197/Ps 5 = 3.20 | 3.82 |
|  | CRM197/Ps 9V = 2.90 | 3.47 |
|  | CRM197/Ps 19F = 3.47 | 4.15 |
| CRM197-1, 14, 19A | CRM197/Ps 1 = 2.87 | 3.43 |
|  | CRM197/Ps 14 = 3.15 | 3.77 |
|  | CRM197/Ps1 9A = 3.45 | 4.13 |
| CRM197-22F, 23F, 33F | CRM197/Ps 22F = 3.25 | 3.89 |
|  | CRM197/Ps 23F = 2.80 | 3.35 |
|  | CRM197/Ps 33F = 3.05 | 3.64 |
| CRM197-4, 6B, 18C | CRM197/Ps 4 = 2.90 | 3.47 |
|  | CRM197/Ps 6B = 3.41 | 4.07 |
|  | CRM197/Ps 18C = 3.10 | 3.71 |

In the exemplified molecular constructs, the Mean of the (w/w) Protein/type-specific Ps ratio is: 3.08±0.24 (7.8%) corresponding to the Mean of the (mol/mol) ratio: 3.69±0.29.

The above examples make evidence that different stoichiometries of synthesis, as addressed by the amount of reagents participating to the chemical equilibrium reported in the above chemical equation, may lead to a molecular construct of different stoichiometry, where the amount of helper T-dependent carrier protein in the molecular construct can be optimally selected according to the optimal expression of immunogenicity of such molecular construct in the various age groups of the human population. In both, above exemplified, 15-valent formulations, containing five molecular constructs each carrying three type-specific Ps, the total amount of carrier protein CRM197 is ca. 5 µg, while the conjugated type-specific Ps are in the amount of ca. 1.0 and ca. 0.3 µg, respectively. Thus, at the dose of CRM197 equivalent to the one present in the Prevnar vaccine for each type-specific Ps conjugated, ca. 2 µg/dose, the total amount of CRM197 here exemplified in the 15-valent formulations would be ca. 10 µg or about 33% of the total amount present in the dose of the 13-valent Prevnar vaccine. Even in the hypothesis of a 23-valent formulation of a conjugate vaccine that would use the molecular model reported here, at comparable amount of protein/dose, the total amount of carrier protein would be significantly lower (ca. 50%) of the amount present in the today's reported 13-valent or 15-valent vaccines formulated by association of separate, single type-specific, conjugate antigens.

Accordingly, it is the purpose of the above reported embodiments to provide evidence of the fact that the disclosed multivalent antigenic molecular construct with built-in epitopes can be synthesized in a broad range of stoichiometric parameters in order to then properly define, in mammalian hosts, the optimal dose of the construct even when considering the different age-groups to be immunized by a broad-spectrum vaccine formulation. It may be here important to recall that past clinical studies had demonstrated that, in adults and toddlers, the immune system could not discriminate, in terms of immunogenicity, among different sizes of the conjugated Ps to the protein carrier CRM197 as well as among multi-point (cross-linked) or mono-point (not cross-linked) models of conjugates (Eby R. et al., in: Modern Approaches to New Vaccines, CSH Ed., 119-123, 1994) even though such studies are not publically available for infants in the range 2-24 months of age.

Example 7: Multivalent Molecular Construct with Built-in Epitopes Based on the Carrier Protein Tetanus Toxoid In addition to the carrier protein CRM197, other well established helper T-dependent carrier proteins may be used in a polyvalent formulation which considers the molecular construct disclosed in this application. As an example, the Applicant has here considered Tetanus Toxoid (TT) as carrier protein, an universal immunogen safely used in paediatric immunization since many decades ago. In contrast to the carrier protein CRM197, TT has never been formulated in a 13 or 15-valent conjugate vaccine, so that the safety of such a potential high-dose protein vaccine in humans remains to be eventually established. Accordingly, the use of the disclosed multi-valent molecular construct for a protein like TT represents a rational approach for limiting the amount of carrier protein in a 13 or 15-valent (or more) possible formulation based on such helper-T dependent carrier protein.

TT is a derivative of the homologous toxin, chemically treated for having the toxin purposely detoxified for a human use of the immunogen. The MW of the purified toxoid is quite comparable to that of the toxin, that is $1.51 \times 10^5$, encompassing 1,375 amino acids. However, among other features, the marked difference between toxoid and toxin resides in the amount of residual primary amino groups from the Lysine residues which remain in the toxoid structure after the chemical detoxification. An average of 50 reactive amino groups are about to be detected in the toxoid or about 50% of those originally present in the structure of the toxin, which work as nucleophylic groups in the coupling reaction with the activated bacterial Ps. When comparing the structure of TT to that of CRM197 in terms of capability to compete in the coupling reaction as nucleophylic reagent, one may determine that TT has ca. 50 amino groups/mole (MW=$1.51 \times 10^5$ for 1,375 aa) while CRM197 has 40 amino groups/mole (MW=$58.5 \times 10^4$ for 535 aa), so that the molar density of them (which we define as "molar nucleophile activity") is 3.6% in TT and 7.5% in CRM197, showing a much higher capability of the latter protein to serve as nucleophylic reagent in a given coupling reaction. However, given the significant difference in the MW of the two proteins (basically a factor=2.6 in favor of TT the molar ratios of the protein carrier, for each of the carried carbohydrate antigens selected in the molecular constructs, may result advantageous for TT when one is willing to limit the amount of carrier protein/dose in a polyvalent formulation. In fact, at comparable weight dose of the two carrier proteins, TT results to be 2.6 times lower than CRM197 on molar basis. In contrast, attention must be paid to the fact that its MW may limit the possibility to obtain a molar ratio TT/type-specific Ps with a value ≥1.0 for the optimal induction of T-helper dependency in the host's immune system.

Here below, the Applicant reports on the physical-chemical features of such molecular construct using TT as carrier protein, synthesized according to the method above used for the CRM197-based molecular construct, with a stoichiometry in the reagents which allows the complete glycosylation of the carrier protein. Such a molecular construct can be considered as the basic component for a polyvalent formulation based on the TT carrier protein:

TABLE 10

| Molecular construct | Average (w/w) ratio TT/Ps | Average molar ratio TT/Ps |
|---|---|---|
| TT-6A, 9V, 23F | TT/Ps 6A = 2.08 | 0.96 |
|  | TT/Ps 9V = 1.90 | 0.90 |
|  | TT/Ps 23F = 2.15 | 1.00 |

In the case of multivalent conjugates of N. meningitidis Ps and H. influenzae Ps, as additional examples, here below is a comparison between the carrier proteins CRM197 and TT highlighting the relevance of the carrier protein in the different constructs (synthesized according to different stoichiometries as allowed by the general chemical equation above reported), as related to their MW in the definition of the molar ratio (protein/Ps), when considering for the protein and the Ps the MW values above reported in Tables 8-9:

TABLE 11

| Molecular construct | Average (w/w) ratio TT/Ps or CRM/Ps | Average molar ratio TT/Ps or CRM/Ps |
|---|---|---|
| TT-A, C, Hib | TT/PsA = 1.79 | 0.83 |
|  | TT/PsC = 2.05 | 0.95 |
|  | TT/PsHib = 1.91 | 0.89 |
| CRM197-A, C, Hib | CRM197/PsA = 2.18 | 2.60 |
|  | CRM197/PsC = 1.87 | 2.24 |
|  | CRM197/PsHib = 1.95 | 2.33 |
| CRM197-A, C, W135, Y | CRM197/PsA = 0.78 | 0.93 |
|  | CRM197/PsC = 0.97 | 1.16 |
|  | CRM197/PsW135 = 0.75 | 0.90 |
|  | CRM197/PsY = 0.88 | 1.05 |

BIBLIOGRAPHY

Arndt and Porro, Immunobiology of Proteins and Peptides, Edited by M. Z. Atassi, Plenum Press, New York and London, pages 129-148, 1991.

Berzofsky J. A. and Schechter A. N. Mol. Immunol., 18: 751-763, 1981.
Besnard J. et al., Nature, 492: 215-220, 2012.
Bromuro, C, et al. (2010). Vaccine 28, 2615-2623.
Calix J. J. et al. J. Bacterid. 193:5271-5278, 2011.
Dagan R. et al., Vaccine 28 (34): 5513-5523, 2010.
Eby R. et al., Modern Approaches to New Vaccines, CSH Eds., 119-123, 1994.
European patent EP 1868645.
European patent EP 1501542.
European Pharmacopoeia 5$^{th}$ Edition (2008).
Giannini G. et al., Nucl. Acid Res., 12, 4063-4069, 1984.
Han, Y. et al. (2000). Infect. Immun. 68, 1649-1654.
Kabat E. A., J. Immunol. 97: 1-11, 1966.
Laemmli U.K., Nature 227, 680-685, 1970.
Moreau M. et al., Carbohydrate Res., 182 (1): 79-99, 1988.
Nanra J. S. et al., Human Vaccines and Immunotherapeutics, 9:3, 480-487, 2013.
O'Riordan K. and Lee J.C., Clin. Microbiol. Rev., 17: 218-234, 2004.
Porro M. et al., J. Infect. Dis., 142 (5), 716-724, 1980.
Porro M. et al., Anal. Biochem. 118: 301-306, 1981.
Porro M. et al. Medecine Iropicale, 43: 129-132, 1983.
Porro M. et al. Molecular Immunology, 22: 907-919, 1985.
Porro M. et al. Molecular Immunology, 23: 385-391, 1986.
Porro M. Edited by R. Bell and G. Torrigiani (WHO), pages 279-306; New York 1987.
Pride M. W. et al., Clin. And Vaccine Immunol. 19 (8): 1131-1141, 2012.
Rebers P. A. and Heidelberger M., J. Am. Chem. Soc, 83: 3056-3059, 1961.
Reeves R. E. and Goebels W. F., J. Biol. Chem., 139: 511-519, 1941.
Richter S. et al., Clin. Infect. Dis., 48:23-33, 2009.
Rustici A. et al., Science 259: 361-365, 1993.
Satzke C. et al., J. Clin. Microbiol., 48(11): 4298, 2010.
Schwebach, J. R., et al. 2002. Infect Immun 70: 2566-2575.
Swanson D., IDSA meeting, Boston, 2011.
Towbin H. et al., PNAS 76: 4350-4354, 1979.
Uchida T. et al., J. Biol. Chem. 248, 3838-3844, 1973.
U.S. Pat. No. 4,711,779.
U.S. Pat. No. 5,306,492.
Xin, H. et al. (2008). Proc. Natl. Acad. Sci. U.S.A. 105, 13526-13531.
Yao K H et al., Diag. Microbiol. Infect. Dis., 70(3):291-8, 2011.
Zucker D. and Murphy J. R., Mol. Immunol. 21, 785-793, 1984.

---

The invention claimed is:

1. A conjugation process for preparing the antigenic multivalent molecular construct consisting of a basic unit comprising a helper-T dependent carrier protein covalently bound to a minimum of three carbohydrate structures which are capsular poly saccharides of different serological specificity by a linker comprising imine reduced bonds and amide bonds, wherein each carbohydrate structure comprises at least one of the repeating basic epitopes consisting of a minimum of five to twelve monosaccharide residues, where said carrier protein is selected from the group consisting of natural diptheria mutant 6 protein CRM197, diptheria toxoid, tetanus toxoid, Protein D from *Haemophilus influenzae*, Pneumonococcal surface proteins, Pneumonoccal toxin and derivatives thereof including tetanus toxoid derivatized by an adipic acid dihydrazide spacer characterized in that at least one mole or fraction thereof of protein carrier carries at least one mole or fraction thereof of each of the at least three different type-specific carbohydrate antigens in a physiologically acceptable vehicle, optionally together with an adjuvant or pharmaceutically acceptable excipients, said conjugation process comprising the following steps:
   a) chemical activation of the at least three antigenically different carbohydrate structures to mono-functionality or polyfunctionality by O-de-hydrogen uncoupling via oxidation and reductive amination forming imine reduced bonds with an alkyl diamine spacer, then derivatized to active esters of said carbohydrate structures;
   b) simultaneously coupling, or a step-by-step coupling, of at least three ester-derivative carbohydrate structures to the amino groups of the polyfunctional carrier protein through the formation of amide bonds;
   wherein at least one mole or fraction thereof of protein carrier is reacted with at least one mole or fraction thereof of each of the at least three different type-specific carbohydrate antigens.

2. The conjugation process according to claim 1, wherein the carbohydrate structures are chemically activated in their corresponding diamine butyric acid derivatives and the active esters are succinimidyl esters.

3. The conjugation process according to claim 1 wherein said polyfunctional carrier protein is CRM197.

4. The conjugation process according to claim 1, wherein said at least three carbohydrate structures are selected among the following triads of polysaccharides from *Streptococcus pneumoniae* 3,6A,7F; 4,5,9V; 1,6B,14; 18C,19A, 23F; 6C,19F,22F; 12F,15B,33F; 5,9V,19F; 1,14,19A; 22F, 23F,33F; 4,6B,18C.

5. The conjugation process for preparing the antigenic multivalent molecular construct according to claim 1, which comprises the simultaneous coupling or the step-by-step coupling of the amino groups of the polyfunctional carrier protein with at least three antigenically different carbohydrate structures, via reductive amination forming imine-reduced bonds, such carbohydrate structures being previously activated to monofunctionality or polyfunctionality, with or without spacers, by O-de-hydrogen uncoupling via oxidation,
   wherein at least one mole or fraction thereof of protein carrier is reacted with at least one mole or fraction thereof of each of the at least three different type-specific carbohydrate antigens.

6. The conjugation process according to claim 1, wherein the carbohydrate structures of step a) comprise at least one of the repeating basic epitopes consisting of a minimum of five to twelve monosaccharide residues as assessed by molecular mass determination and NMR spectroscopy, said repeating basic epitopes being antigenically assessed by reactivity with type-specific or group-specific polyclonal or monoclonal antibodies through the determination of their respective MIC50 values in the inhibition of their homologous Polysaccharide-Antibody reference system.

7. The antigenic multivalent molecular construct obtainable through the conjugation process according to claim 1.

* * * * *